United States Patent
Yamamoto et al.

(10) Patent No.: US 8,193,304 B2
(45) Date of Patent: Jun. 5, 2012

(54) BENZOBISTHIAZOLE COMPOUND, BENZOBISTHIAZOLE POLYMER, ORGANIC FILM INCLUDING THE COMPOUND OR POLYMER AND TRANSISTOR INCLUDING THE ORGANIC FILM

(75) Inventors: Satoshi Yamamoto, Yokohama (JP); Masafumi Torii, Yokohama (JP); Tamotsu Aruga, Atsugi (JP); Tamotsu Horiuchi, Tagata-gun (JP); Takuji Kato, Fukuoka (JP); Toshiya Sagisaka, Yokohama (JP); Takashi Okada, Yokohama (JP); Daisuke Goto, Yokohama (JP); Shinji Matsumoto, Yokohama (JP); Hiroshi Ikuno, Yokohama (JP); Takeshi Orito, Yokohama (JP); Masataka Mohri, Yokohama (JP)

(73) Assignee: Ricoh Company Limited, Tokyo (JP)

(*) Notice: Subject to any disclaimer, the term of this patent is extended or adjusted under 35 U.S.C. 154(b) by 126 days.

(21) Appl. No.: 12/356,810

(22) Filed: Jan. 21, 2009

(65) Prior Publication Data

US 2009/0230386 A1    Sep. 17, 2009

(30) Foreign Application Priority Data

Jan. 22, 2008 (JP) ................... 2008-011190
Aug. 29, 2008 (JP) ................... 2008-221131

(51) Int. Cl.
    *C08G 75/00*    (2006.01)
(52) U.S. Cl. ............................ 528/377; 528/380
(58) Field of Classification Search ............ 528/373, 528/380
    See application file for complete search history.

(56) References Cited

U.S. PATENT DOCUMENTS

| | | |
|---|---|---|
| RE33,155 E | 1/1990 | Akutsu et al. |
| 5,233,017 A | 8/1993 | Dotrong et al. |
| 7,166,689 B2 | 1/2007 | Sagisaka et al. |
| 7,183,418 B2 | 2/2007 | Heeney et al. |
| 7,232,750 B1 | 6/2007 | Kingsborough |
| 2007/0092760 A1 | 4/2007 | Sagisaka et al. |

FOREIGN PATENT DOCUMENTS

| | | |
|---|---|---|
| JP | 5-55568 | 3/1993 |
| JP | 2005-76030 | 3/2005 |
| JP | 2005-101493 | 4/2005 |
| JP | 2005-206750 | 8/2005 |
| JP | 2005206750 | * 8/2005 |

OTHER PUBLICATIONS

U.S. Appl. No. 11/816,437, filed Aug. 16, 2007, Takumi Yamaga, et al.
Itaru Osaka, et al., "Novel Thiophene-Thiazolothiazole Copolymers for Organic Field-Effect Transistors", Advanced Materials 2007, 19, pp. 4160-4165.
Hao Pang, et al., "Advantageous 3D Ordering of π-Conjugated Systems: a New Approach Towards Efficient Charge Transport in any Direction", Advanced Materials 2007, 19, pp. 4438-4442.
Tanaka Tatsuo, et al., "Organic semiconductor materials, organic (field-effect) transistors, switching devices, and 5-membered heterocycles therefor", Database CA [Online], Chemical Absracts service, XP002527356, Aug. 4, 2005, 3 Pages.
Zitao Liu, et al., "Structure-Variant Exciton Transfer and Spatial Confinement in Statistical Copolymers and Blends Based on Polybenzazoles", Chemistry of Materials, vol. 19, No. 5, XP002527355, Jan. 26, 2007, pp. 1164-1169.

\* cited by examiner

*Primary Examiner* — Randy Gulakowski
*Assistant Examiner* — Shane Fang
(74) *Attorney, Agent, or Firm* — Oblon, Spivak, McClelland, Maier & Neustadt, L.L.P.

(57) ABSTRACT

A benzobisthiazole compound having a specific formula, and a benzobisthiazole polymer having a specific benzothiazole structure. An organic film including the benzobisthiazole polymer, the benzobisthiazole compound and/or a polymer obtained from the benzobisthiazole compound. An organic thin-film transistor including an organic semiconductor layer including the organic film; a pair of electrodes configured to flow an electric current through the organic semiconductor layer; and a third electrode configured to apply a voltage to the organic semiconductor layer.

6 Claims, 7 Drawing Sheets

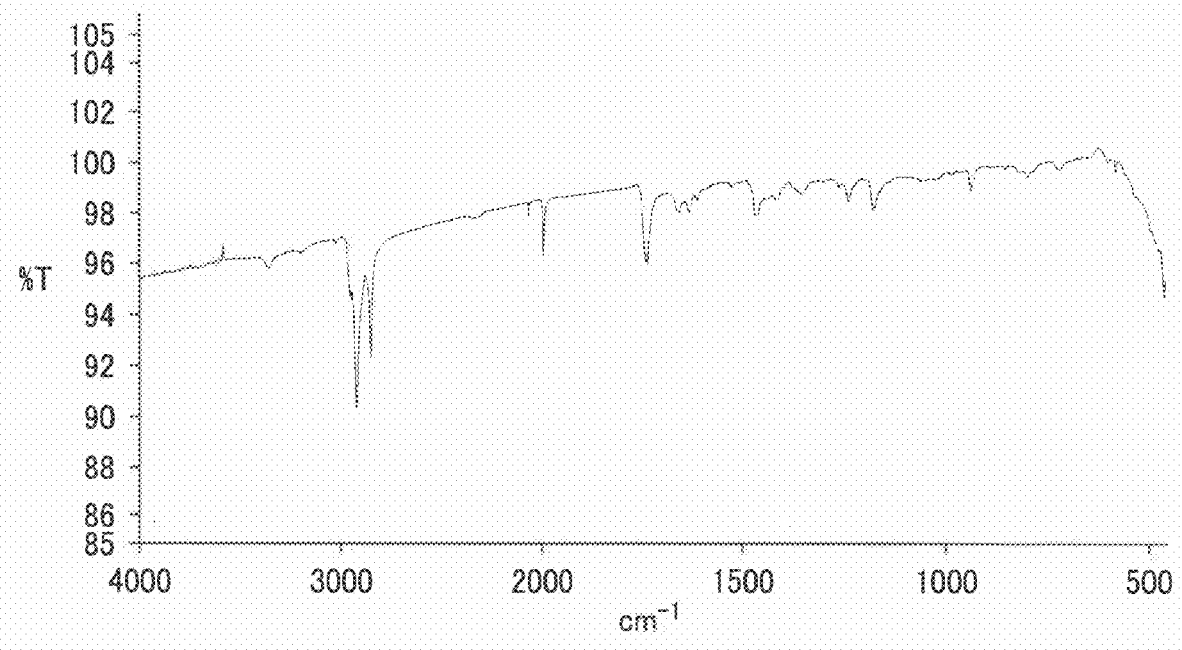

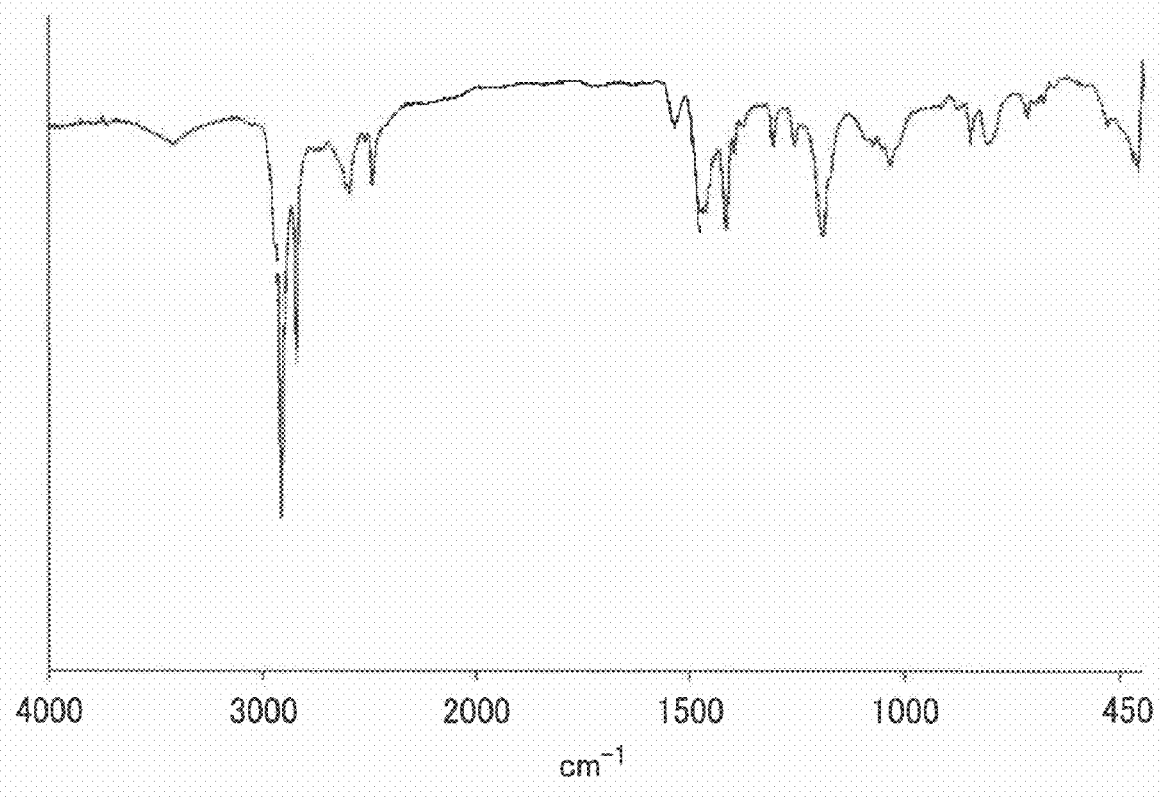

BENZOBISTHIAZOLE COMPOUND, BENZOBISTHIAZOLE POLYMER, ORGANIC FILM INCLUDING THE COMPOUND OR POLYMER AND TRANSISTOR INCLUDING THE ORGANIC FILM

BACKGROUND OF THE INVENTION

1. Field of the Invention

The present invention relates to a benzobisthiazole compound and a benzobisthiazole polymer. In addition, the present invention also relates to an organic film including the benzobisthiazole compound, the benzobisthiazole polymer or a polymer obtained from the benzobisthiazole compound. Further, the present invention also relates to a transistor including the organic film.

2. Discussion of the Background

Recently, research and development concerning organic electronic devices using an organic semiconductor material have been actively made. Organic semiconductor materials have an advantage over inorganic semiconductor materials such that a thin film can be easily formed using a simple wet method such as printing methods and spin coating methods, and thereby the process for preparing a thin film transistor using an organic semiconductor material can be performed at a relatively low temperature compared to those in the cases of thin film transistors using an inorganic semiconductor material. Therefore, it becomes possible to form such an organic thin film even on a plastic substrate, which has a relatively low heat resistance compared to those of inorganic substrates. Accordingly, light-weight and low-cost electronic devices (such as displays) can be provided by using such an organic thin film. In addition, flexible electronic devices can be provided by using such an organic thin film. Thus, the applications of the organic thin films are broadening.

Various organic thin film transistors using a low molecular weight material or a polymer material have been disclosed. With respect to organic thin film transistors using a low molecular weight material, the following materials have been disclosed:

(1) Acene compounds such as pentacene compounds (Synth. Met., 51, 419, 1992, and published unexamined Japanese application No. (hereinafter JP-A) 05-55568);
(2) Phthalocyanine compounds (Appl. Phys. Lett., 69, 3066, 1996);
(3) Fullerene compounds (JP-A 08-228034 corresponding to UP patent No. 6278127, and Appl. Phys. Lett., 67, 121, 1995);
(4) Anthradithiophene compounds (JP-A 11-195790 corresponding to U.S. Pat. No. 5,936,257);
(5) Thiophene oligomers (JP-A 08-228035 corresponding to U.S. Pat. No. 5,574,291, and Chem. Mate., 4, 457, 1998); and
(6) Bisdithienothiophene (Appl. Phys. Lett., 71, 3871, 1997).

With respect to organic thin film transistors using a polymer material, the following materials have been disclosed:
(1) Polythiophene (Appl. Phys. Lett., 69, 4108, 1996); and
(2) Polythienylenevinylene (Appl. Phys. Lett., 63, 1372, 1993).

However, the films prepared by such low molecular weight materials as mentioned above have poor stability, and the films prepared by such polymer materials as mentioned above have poor qualities due to low purity. Therefore, it is desired to make improvement thereto.

As mentioned above, acene compounds typified by pentacene have been proposed as organic semiconductor materials, for example, in JP-A 05-55568. It is described therein that organic thin film transistors using pentacene for their organic semiconductor layers have a relatively high mobility (i.e., carrier mobility). However, such acene compounds have very poor solubility in popular solvents. Therefore, when a thin layer of an acene compound is formed for forming an active layer of an organic thin film transistor, a vacuum evaporation method has to be used. Namely, simple methods such as printing and coating cannot be used for forming a thin layer of an acene compound. Therefore, acene compounds do not fulfill the need.

It is described in Science, 2004, 303, 5664, 1644-1646 that one of acene compounds, rubrene, has a high solubility in solvents, and a single crystal of rubrene has a very high mobility. However, a film of rubrene, which is prepared by casting a solution of rubrene, does not have a single crystal structure, and therefore the mobility of the film is not sufficient for organic thin film transistors. In other words, a layer of a single crystal rubrene cannot be prepared by a simple method.

It is described in Synth. Met. 84, 269 (1997) that poly(3-alkylthiophene) is used as polymer organic semiconductor materials. Since a regioselective alkyl group is incorporated in the polymeric organic semiconductor materials, the materials are soluble in solvents, although the solubility is low. Therefore, they manage to prepare a thin film of such a polymeric organic semiconductor material using a simple method such as coating and printing.

On the other hand, in order that organic electronic devices stably operate, the organic semiconductor materials used therefor are required to have good oxidative stability. Although a thin film of poly(3-alkylthiophene) can be prepared by a simple method such as coating and printing, the resultant film tends to be easily oxidized because of having a low ionization potential. Therefore, organic thin film transistors using poly(3-alkylthiophene) for the active layer thereof unstably operate in the air. It is described in Synth. Met. 84, 269 (1997) that thieno[2,3-b]thiophene is incorporated in poly(3-alkylthiophene) in such a manner that the conjugated system of the polymer is cut, to improve the oxidative stability of the polymer. Although the proposed compounds have relatively good oxidative stability, the compounds have drawbacks such as insufficient carrier mobility and ON/OFF ratio due to cut of the conjugated system.

JP-A 2005-206750 discloses organic semiconductor materials having a condensed ring including a hetero atom and transistors using the materials in attempting to impart a good combination of carrier mobility and preservability thereto. However, the organic semiconductor materials have poor solubility in solvents, and therefore such simple methods as mentioned above cannot be used for forming thin layers thereof. Namely, organic semiconductor materials having a good combination of solubility, oxidative stability, carrier mobility and ON/OFF ratio cannot be provided.

In addition, it is described in Adv. Mater., 2007, 19, 4160-4165 and 4438-4442 that organic semiconductor materials having a condensed ring including a hetero atom such as thiazole derivatives (e.g., thiazolothiazole and benzobisthiazole) have good stability in the air because the thiazole skeleton has good resistance to oxygen. Further, it is described therein that by extending the π-conjugated system, donor-acceptor interaction is caused between a thiazole unit serving as an acceptor and a thiophene ring serving as a donor, thereby accelerating intermolecular charge transfer. However, even such thiazole compounds have the following drawbacks:

(1) When the thiazole compounds are low molecular weight compounds, layers having good stability cannot be formed; and (2) When the thiazole compounds are polymers, the polymers have insufficient qualities in view of purity and variation of polymerization degree and controlling of polydispersity.

Because of these reasons, a need exists for an organic semiconductor material having good combination of solubility, oxidative stability, carrier mobility and ON/OFF ratio.

SUMMARY OF THE INVENTION

As an aspect of the present invention, a benzobisthiazole polymer having the following formula (1) is provided.

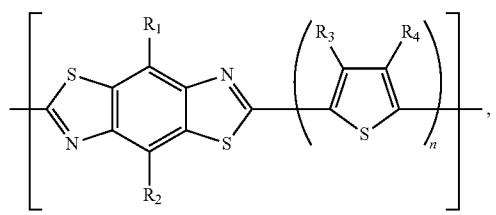

(1)

wherein each of $R_1$, $R_2$, $R_3$ and $R_4$ represents a hydrogen atom, a halogen atom, a substituted or unsubstituted alkyl group, a substituted or unsubstituted alkoxyl group, or a substituted or unsubstituted thioalkoxyl group, wherein at least one of $R_1$, $R_2$, $R_3$ and $R_4$ is not a hydrogen atom; and n is a positive integer (i.e., an integer of not less than 1), wherein when n is 2 or more, each of $R_3$ may be the same as or different from the others and each of $R_4$ may be the same as or different from the others.

It is preferable that the polymer has the following formula (2):

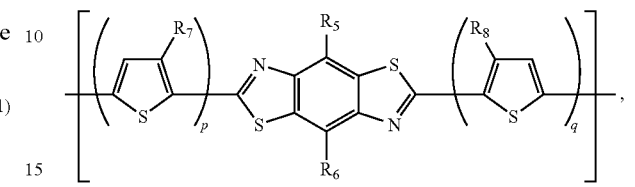

(2)

wherein each of $R_5$, $R_6$, $R_7$ and $R_8$ is a hydrogen atom, a halogen atom, a substituted or unsubstituted alkyl group, a substituted or unsubstituted alkoxyl group or a substituted or unsubstituted thioalkoxyl group, wherein at least one of $R_5$, $R_6$, $R_7$ and $R_8$ is not a hydrogen atom; and each of p and q is a positive integer, wherein when p is 2 or more, each of $R_7$ may be the same as or different from the others, and when q is 2 or more, each of $R_8$ may be the same as or different from the others.

Alternatively, a benzobisthiazole compound having the following formula (3) is provided.

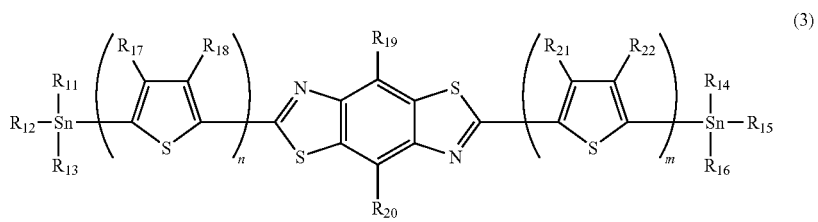

(3)

wherein each of $R_{11}$ to $R_{22}$ represents a hydrogen atom, a halogen atom, a substituted or unsubstituted alkyl group, a substituted or unsubstituted alkoxyl group, or a substituted or unsubstituted alkylthio group; and each of m and n is 0 or a positive integer, wherein when m is 2 or more, each of $R_{21}$ may be the same as or different from the others, and each of $R_{22}$ may be the same as or different from the others, and wherein when n is 2 or more, each of $R_{17}$ may be the same as or different from the others, and each of $R_{18}$ may be the same as or different from the others.

The benzobisthiazole compound preferably has the following formula (4).

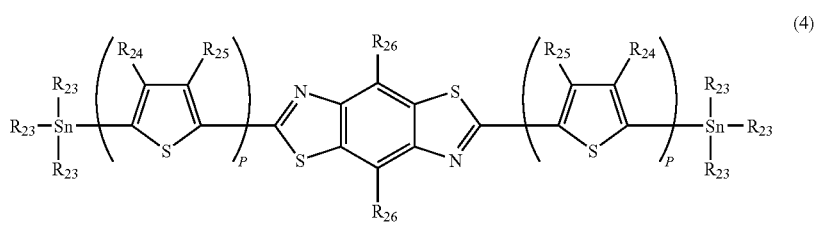

(4)

wherein $R_{23}$ represents a substituted or unsubstituted alkyl group; each of $R_{24}$, $R_{25}$ and $R_{26}$ represents a hydrogen atom, a halogen atom, a substituted or unsubstituted alkyl group, a substituted or unsubstituted alkoxyl group, or a substituted or unsubstituted thioalkoxyl group; and p is 0 or a positive integer, wherein when p is 1 or more, each of $R_{24}$ is the same as or different from the others, and each of $R_{25}$ is the same as or different from the others.

As another aspect of the present invention, an organic film is provided, which includes a benzobisthiazole polymer having formula (1), a benzobisthiazole compound having formula (3) and/or a polymer obtained from a benzobisthiazole compound having formula (3).

As yet another aspect of the present invention, an organic thin-film transistor is provided, which includes:

an organic semiconductor layer including the organic film;

a pair of electrodes configured to flow an electric current through the organic semiconductor layer; and a third electrode configured to apply a voltage to the organic semiconductor layer.

BRIEF DESCRIPTION OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein:

FIG. 4 the IR spectrum of a second example of the benzobisthiazole polymer of the present invention;

FIG. 11 is the IR spectrum of a comparative benzobisthiazole polymer prepared by a conventional method.

DETAILED DESCRIPTION OF THE INVENTION

Figure 1A:
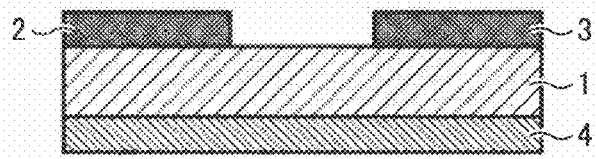
FIGS. 1A-1D are schematic cross-sectional views illustrating examples of the organic thin film transistor of the present invention.
Figure 1B:
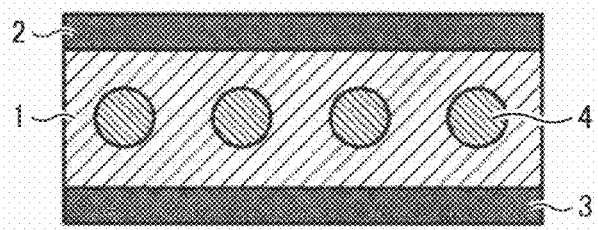
Figure 1C:
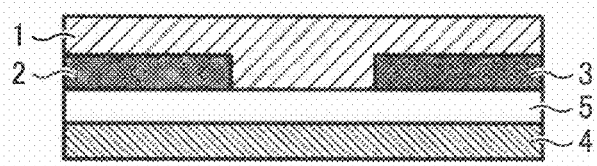

At first, the benzobisthiazole polymer of the present invention will be explained.

The benzobisthiazole polymer of the present invention has good combination of solubility, oxidative stability (stability in the air), mobility and ON/OFF ratio.

It has been proposed that polymers having a phenylenebenzo[1,2-d; 4,5-d']bisthiazole skeleton can be preferably used as heat resistant polymers because the benzo[1,2-d; 4,5-d']bisthiazole skeleton has a high oxidation potential and good heat resistance. In addition, it is described in Macromolecules, 2001, 34, 2012-2014 that due to steric hindrance caused by the benzo[1,2-d; 4,5-d']bisthiazole moiety and the phenylene moiety, the polymers do not have planarity. In this case, the polymers are rigid and have a good combination of heat stability and oxidative stability. However, such structure is disadvantageous for extension of the π-conjugated system. Therefore, the polymers are not expected to have a good combination of mobility and ON/OFF ratio.

JP-A 2005-206750 discloses polymers having only a unit with a benzobisthiazole skeleton, alternative copolymers including a unit having a benzobisthiazole skeleton and a unit having a 2,5-dialkylphenylene group, and copolymers including a unit in which two continuous benzobisthiazole skeletons and a unit having a 1,2-bisthioethylene group are alternately arranged, as organic semiconductor materials. However, the details of polymers in which a benzo[1,2-d; 4,5-d']bisthiazole skeleton is connected with a thiophene skeleton are not disclosed therein. In addition, since the phenylene ring is adjacent to the benzo[1,2-d; 4,5-d']bisthiazole skeleton, or the benzothiazole skeletons are not directly connected with each other because the 1,2-bisthioethylene group is present therebetween, the resultant polymers are not expected to have a good combination of mobility and ON/OFF ratio.

Polythiophenes typified by poly(3-alkylthiophene) have a high planarity, but have a drawback in that the oxidation potential is relatively high. The present inventors discover that by arranging a benzo[1,2-d; 4,5-d']bisthiazole skeleton and a thiophene group so as to be adjacent to each other, a high planarity and a proper oxidation potential can be imparted to the resultant polymers without preventing extension of the π-conjugated system. In addition, it is discovered that polymers having the repeat units mentioned above for use in the present invention are rigid, and the polymers can easily have an aggregation structure upon application of a thermal stimulation (such as annealing treatments) thereto, wherein the annealed polymers have higher mobility and ON/OFF ratio than the non-annealed polymers.

The reason why the annealed polymers have higher mobility is considered to be that due to the rigidity of the polymers, the molecules of the polymers effectively form aggregates due to molecular motion thereof caused by the thermal stimulation, thereby improving the mobility. In addition, by stereoregularly incorporating a soluble group typified by alkyl groups in such rigid polymers, organic films achieving a regular aggregated state (such as crystallinity/liquid-crystallinity/orientation) can be advantageously formed. Polymers in such high stereoregularity state tend to have a higher mobility than the polymers in an amorphous state.

In the present application, a polymer having a high "stereoregularity (i.e., a stereo-regularly ordered structure)" is defined as a polymer having a repeat unit with good symmetric property, i.e., a polymer in which the same symmetric structure is repeated at a constant frequency. In this regard, monomers used for preparing the polymer have symmetric property or the resultant copolymers have symmetric property if the monomers used do not have symmetric property. By using a polymer having a repeat unit with good symmetric property, an organic film achieving high stereoregularity (such as crystallinity/liquid-crystallinity/orientation) can be formed while maintaining the conjugated plane structure of the polymer. Therefore, the organic film has high mobility.

When the polymer of the present invention is prepared, condensation polymerization methods can be used. In this regard, proper condensation polymerization methods are selected depending on the groups concerned with the condensation polymerization. Specific examples of the condensation polymerization methods include methods in which appropriate monomers are polymerized using the Suzuki coupling reaction; methods in which appropriate monomers are polymerized using the Grignard reaction; methods in which appropriate monomers are polymerized using the Stille coupling reaction; methods in which appropriate monomers are polymerized using a Ni(0) complex (zerovalent nickel complex); methods in which monomers are polymerized using an antioxidant such as $FeCl_3$; electrochemical oxidation polymerization methods; etc. Among these methods, methods using the Suzuki coupling reaction, Grignard reaction, Stille coupling reaction or zerovalent nickel complex are preferably used because the structure of the resultant polymers can be easily controlled.

Suitable groups of monomers concerned with the condensation polymerization reactions change depending on the condensation polymerization reactions for which the monomers are used. For example, when a zerovalent nickel complex is used (i.e., when a method such as the Yamamoto reaction is used), suitable groups include halogen atoms, alkylsulfonate groups, arylsulfonate groups, and arylalkylsulfonate groups. When a nickel catalyst or a palladium catalyst is used (i.e., when a method such as the Suzuki coupling reaction is used), alkylsulfonate groups, halogen atoms, boric ester groups, and —$B(OH)_2$ group are preferably used.

The halogen atom of aryl halogenated compounds is preferably an iodine or bromine atom (i.e., iodinated or brominated materials) in view of reactivity.

One example of the methods using the Grignard reaction is as follows. Specifically, a halogenated compound is reacted with magnesium metal in an ether solvent such as tetrahydrofuran, diethyl ether, and dimethoxy ethane to prepare a Grignard reagent solution. The thus prepared Grignard reagent solution is then mixed with a monomer solution. After carefully adding a nickel or palladium catalyst to the mixture to prevent occurrence of an excessive reaction, the mixture is heated while refluxed to perform the reaction. The added amount of the Grignard reagent is not less than the same equivalent weight as that of the monomers used, preferably from 1 to 1.5 times the equivalent weight of the monomers, and more preferably from 1 to 1.2 times the equivalent weight of the monomers. When the methods other than these methods are used, the reactions are performed using known methods.

Specific examples of the arylboronic compounds for use in the Suzuki coupling reaction include esters of arylboronic acid (arylboronic esters), and salts of arylboronic acid. Among these compounds, arylboronic esters are preferably used because the compounds have a high crystallinity while being easily refined and the compounds do not form a trihydrate compound (boroxin) unlike arylboronic acid. Arylboronic esters can be synthesized, for example, by the following methods:

(1) Methods in which arylboronic acid and an alkyldiol are heated in a dehydrated organic solvent to be reacted;
(2) Methods in which the halogen moiety of an arylhalogenated compound is metalized, and then an alkoxyboronic ester is added thereto;
(3) Methods in which a Grignard reagent of an arylhalogenated compound is prepared, and then an alkoxyboronic ester is added thereto; and
(4) Methods in which an arylhalogenated compound and bis(pinacolate) diboron or bis(neopentyl glycolate) diboron are heated in the presence of a palladium catalyst to be reacted.

Specific examples of the palladium catalysts include $Pd(PPh_3)_4$, $PdCl_2(PPh_3)_2$, $Pd(OAc)_2$, $PdCl_2$, combinations of palladium carbon with triphenylphosphine serving as a ligand. Among these catalysts, $Pd(PPh_3)_4$ is preferably used.

Bases are essential for the Suzuki coupling reaction, and relatively weak bases such as $Na_2CO_3$, $NaHCO_3$, and $K_2CO_3$ can produce good results. When the reaction is affected by steric hindrance, relatively strong bases such as $Ba(OH)_2$, and $K_3PO_4$ can produce good results. Other bases such as sodium hydroxide, potassium hydroxide, metal alkoxides (e.g., potassium t-butoxide, sodium t-butoxide, lithium t-butoxide, potassium 2-methyl-2-butoxide, sodium 2-methyl-2-butoxide, sodium methoxide, sodium ethoxide, potassium methoxide, and potassium ethoxide), etc.

In order to smoothly perform the Suzuki coupling reaction, phase transfer catalysts can be used. Suitable phase transfer catalysts include tetraalkyl halogenated ammonium, tetraalkyl ammonium bisulfate, etc. Specific examples of preferable phase transfer catalysts include tetra-n-butylhalogenated ammonium, benzyltrimethylhalogenated ammonium, tricaprylylmethyl ammonium chloride, etc.

Specific examples of the solvents for use in the Suzuki coupling reaction include alcohols and ethers such as methanol, ethanol, isopropanol, butanol, 2-methoxyethanol, 1,2-dimethoxyethane, and bis(2-methoxyethyl)ether; ring ethers such as dioxane, and tetrahydrofuran; other solvents such as benzene, toluene, xylene, dimethylsulfoxide, N,N-dimethylformamide, N-methylpyrrolidone, 1,3-dimethyl-2-imidazolidinone, etc.

Suitable zerovalent nickel complexes for use in the Yamamoto reaction include bis(1,5-cyclooctadiene)nickel(0), ethylenebis(triphenylphosphine)nickel(0), tetrakis(triphenylphosphine) nickel(0), etc. Among these materials, bis(1,5-cyclooctadiene)nickel(0) is preferably used.

The reaction temperature at which the polymerization reaction is performed is determined depending on the reactivity of the monomers used, and the properties of the solvents used for the reaction, but is preferably not higher than the boiling point of the solvent used for the reaction.

The reaction time of the polymerization reaction is also determined depending on the reactivity of the monomers used, and the targeted molecular weight of the polymer, but is generally from 2 to 50 hours and preferably from 5 to 24 hours.

In order to control the molecular weight of the polymer, a reaction stopping agent such as molecular weight controlling agents and sealants serving as a terminal group for sealing the end of the polymer can be included in the reacting system. It is possible to add such reaction stopping agents at the beginning of the reaction. Therefore, the polymer of the present invention can include a group of such a reaction stopping agent at the end position thereof. Compounds having only one reactive group can be used as the reaction stopping agents, and specific examples of such reaction stopping agents include phenylboronic acid, bromobenzene, iodobenzene, etc.

The molecular weight (i.e., polystyrene-conversion number average molecular weight) of the polymer of the present invention is preferably from 1,000 to 1,000,000, and more preferably from 2,000 to 500,000. When the molecular weight is too low, the film of the polymer tends to form cracks, and thereby the film cannot be practically used. In contrast, when the molecular weight is too high, the solubility of the polymer in general organic solvents decreases. Therefore, the viscosity of the coating liquid seriously increases, resulting in impossibility of coating of the coating liquid.

In order to improve the mechanical properties of the resultant polymer, a small amount of one or more chain branching agents can be added in the polymerization reaction. Suitable chain branching agents include compounds having three or more polymerizable reactive groups, which are the same as or different from each other.

The thus prepared polymer of the present invention is used after removing impurities such as bases used for the polymerization reaction, unreacted monomers, reaction stopping agents, and inorganic salts produced in the polymerization reaction. Suitable methods for use in removing such impurities include known methods such as reprecipitation, extraction, Soxhlet extract, ultrafiltration, dialysis, etc.

Specific examples of the thus prepared polymer having formula (1) (i.e., the repeat units of the polymer) include the following compounds (1)-1 to (1)-6 in Table 1 below.

TABLE 1

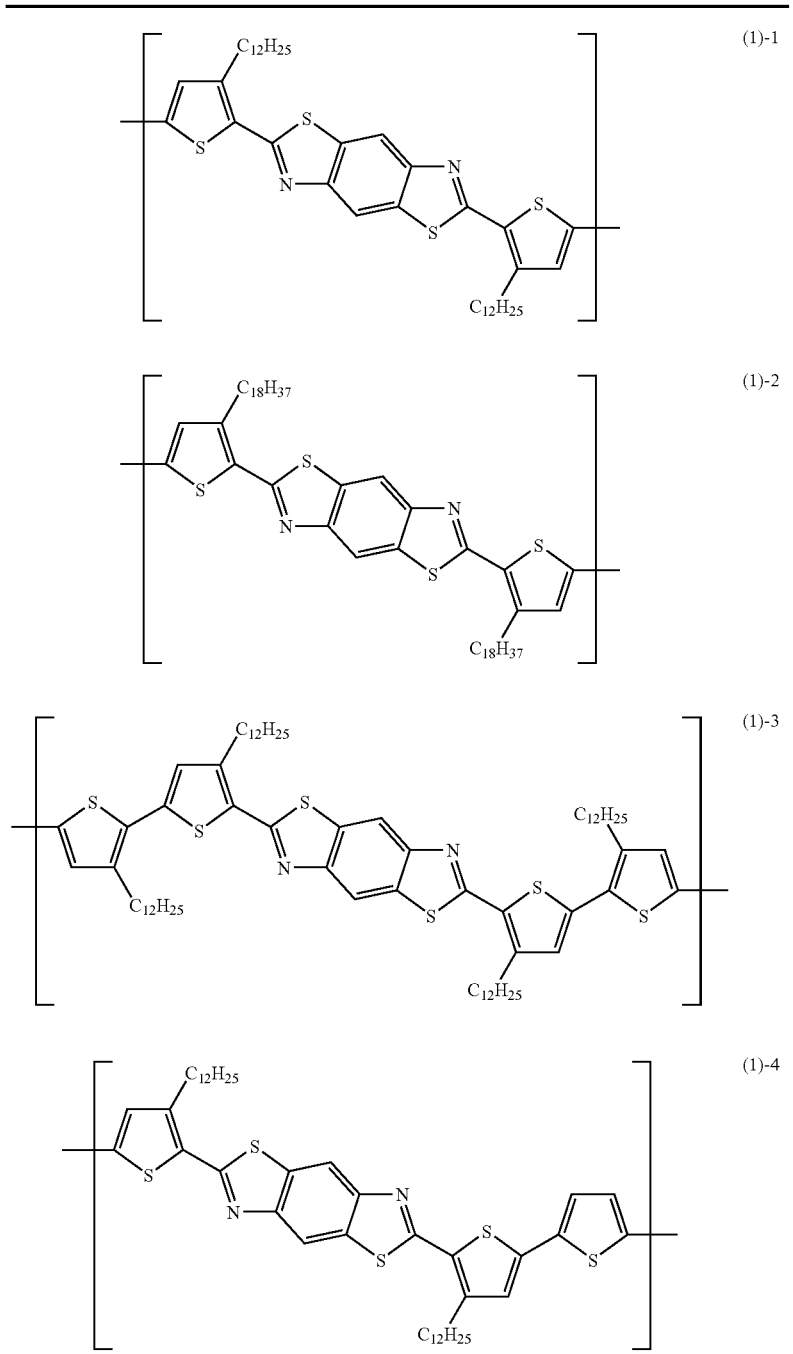

TABLE 1-continued

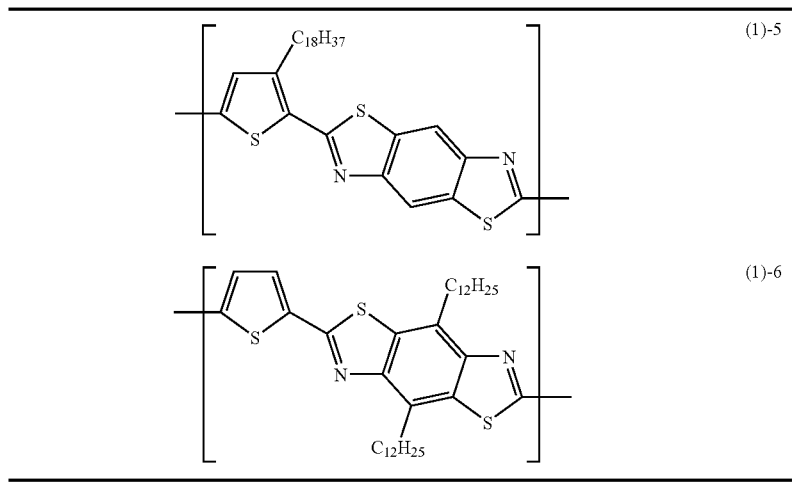

Several synthesis Examples of the polymer will be explained in detail, but the synthesis method is not limited thereto.

Synthesis Example 1

2-Thienobenzo[1,2-d; 4,5-d']bisthiazole is derived from 2-carboxylthiophene. As illustrated in the below-mentioned reaction formula, it is possible to synthesize the compound using an organic alkali metal such as n-BuLi, followed by adding dry ice thereto. Alternatively, it is possible to use the method using Mg as disclosed in Macromolucules 2007, 40, 6585-6593.

In order to perform a condensation reaction of 2-carboxylthiophene and 2,5-diamino-1,4-benzenethiol, a method disclosed in Chem. Mater. 2004, 16, 4286-4291, in which an acid chloride is formed by reacting 2-carboxylthiophene with thionyl chloride, and then a polymerization reaction is performed using an Eaton's reagent can be used. Alternatively, a method disclosed in Macromolecules, 1996, 29, 3787-3792, in which a condensation reaction is performed using polyphosphoric acid (PPA) and sulfolane, can also be used. Since the thus prepared 2-thienobenzo[1,2-d; 4,5-d']bisthiazole derivative is hardly oxidized, the oxidation polymerization reaction using $FeCl_3$ hardly proceeds. Therefore, it is preferable to produce a halogenated compound of the compound as illustrated in the below-mentioned reaction formula. When homopolymers are prepared using the polymerization methods, the Yamamoto reaction or Grignard reaction can be used. In contrast when copolymers are prepared, popular polymerization reactions such as the Suzuki coupling reaction and the Stille coupling reaction can be used. In the reaction formula below, the parenthetic unit represents a repeat unit of a polymer.

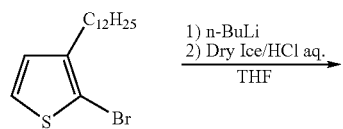

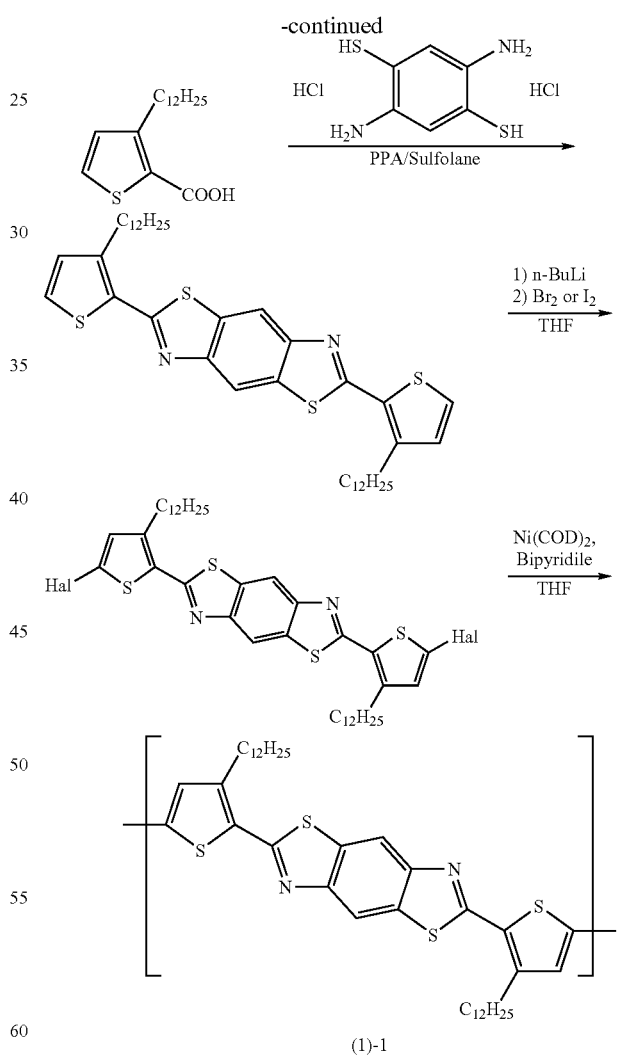

Synthesis Example 2

As disclosed in Macromolecules 2006, 39, 2823-2831, the above-mentioned compounds (i.e., polymers) (1)-3 and (1)-4 can be synthesized by reacting a di-halogen monomer and a bistrimethyl tin compound using the Stille coupling method.

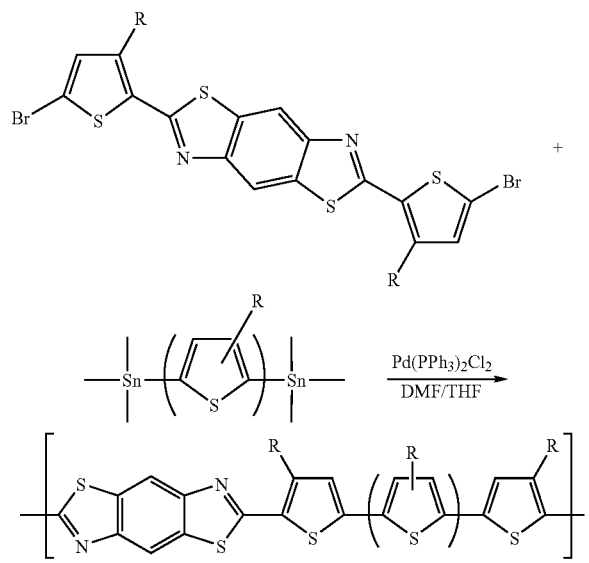

Synthesis Example 3

The polymer of the present invention can be prepared using a condensation reaction of a dicarboxylic acid monomer or a dicarboxylic acid chloride monomer with 2,5-diamino-1,4-benzenethiol dihydrochlorides as illustrated in the following reaction formula.

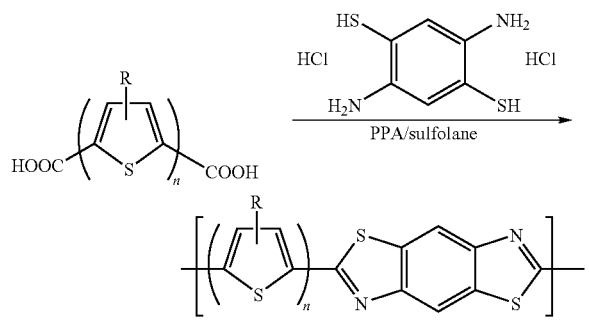

Alternatively, a method disclosed in Chem. Mater. 2004, 16, 4286-4291, in which dicarboxylic acid intermediate is converted to an acid chloride using thionyl chloride, and then the acid chloride is subjected to a polymerization reaction using an Eaton's reagent, can also be used. In addition, a polymerization method disclosed in Macromolecules, 1996, 29, 3787-3792, which uses polyphosphoric acid (PPA) and sulfolane, can also be used.

When removing hydrochloric acid from 2,5-diamino-1,4-benzenethiol dihydrochlorides, polyphosphoric acid (PPA) or an Eaton's reagent is used. However, these compounds typically have low solubility in thiophene compounds. Therefore, the polymerization reaction may be performed using a popular organic solvent such as tetrahydrofuran, toluene, dichloromethane, chloroform, ethyl acetate, dimethylsulfoamide, etc.

The 2-thienobenzo[1,2-d; 4,5-d']bisthiazole polymer of the present invention can include a substituent on an aromatic ring. Specific examples of the substituents include halogen atoms, substituted or unsubstituted alkyl groups, substituted or unsubstituted alkoxyl groups, and substituted or unsubstituted alkylthio groups. In view of solubility of the polymer in solvents, it is preferable for the polymer to have a substituted or unsubstituted alkyl group, a substituted or unsubstituted alkoxyl group, and/or a substituted or unsubstituted alkylthio group. When such a substituent is incorporated in the polymer, the solubility improves as the number of carbon atoms of the substituent increases, but the properties thereof such as charge transportability tend to deteriorate. Therefore, it is preferable to select one or more substituents while considering the solubility and the properties of the resultant polymer. Specific examples of the preferable substituents include alkyl groups, alkoxyl groups and alkylthio groups each having 1 to 25 carbon atoms. In this regard, one or more substituents can be incorporated. When plural substituents are incorporated, the substituents may be the same as or different from each other. In addition, such substituents can optionally have one or more substituents such as halogen atoms, and cyano, aryl, hydroxyl, and carboxyl groups. In this regard, the aryl groups may be further substituted with one or more linear, branched or cyclic alkyl groups, alkoxyl groups and/or alkylthio groups each having from 1 to 12 carbon atoms.

Specific examples of the alkyl groups include methyl, ethyl, n-propyl, i-propyl, t-butyl, s-butyl, n-butyl, i-butyl, pentyl, hexyl, heptyl, octyl, nonyl, decyl, 3,7-dimethyloctyl, 2-ethylhexyl, trifluoromethyl, 2-cyanoethyl, benzyl, 4-chlorobenzyl, 4-methylbenzyl, cyclopentyl, and cyclohexyl groups. Specific examples of the alkoxyl and alkylthio groups include alkoxyl and alkylthio groups, in which an oxygen atom or a sulfur atom is incorporated into the bonding position of the alkyl groups mentioned above, wherein the alkyl groups are bonded with the polymer or substituents at the binding position.

By incorporating a group such as alkyl, alkoxyl and alkylthio groups into the polymer of the present invention, the solubility of the polymer in solvents can be enhanced. By enhancing the solubility of the polymer, devices such as photoelectric transducers, thin film transistors, light emitting diodes can be prepared by a wet film forming method. Therefore, flexibility in preparing the devices (i.e., processibility) can be improved. Specifically, enhancing the solubility of the polymer brings advantages such that various solvents can be used for the coating liquid of the polymer; a solution of the polymer for use in preparing the coating liquid can be prepared in a wide temperature range; and the coated liquid can be dried in a wide temperature range and in a wide pressure range. Therefore, a thin film of the polymer with a high purity and good uniformity can be prepared.

Organic films of the polymer of the present invention can be prepared by known methods such as spin coating methods, casting methods, dip coating methods, inkjet methods, doctor blade coating methods, screen printing methods, and spray coating methods. By using such methods, it become possible to prepare organic films having good properties such as mechanical strength, toughness, and durability without forming cracks in the films. Therefore, the organic films can be preferably used for organic electronic devices such as photoelectric transducers, FET elements, and light emitting elements.

Organic Film Forming Method

Films of the polymer (i.e., organic semiconductor material) of the present invention are typically prepared by coating a coating liquid, which is prepared by dissolving the polymer in a solvent such as dichloromethane, tetrahydrofuran, chloroform, toluene, dichlorobenzene, and xylene, on a substrate.

Specific examples of the coating methods include spray coating methods, spin coating methods, blade coating methods, dip coating methods, cast coating methods, roll coating methods, bar coating methods, die coating methods, inkjet methods, dispense methods, etc. In this regard, a proper method and a proper solvent are selected in consideration of the properties of the polymer used. Suitable materials for use as the substrate on which a film of the polymer of the present invention is formed include inorganic substrates such as glass plates, silicon plates, ITO plates, and FTO plates, and organic substrates such as plastic plates (e.g., PET films, polyimide films, and polystyrene films), which can be optionally subjected to a surface treatment. It is preferable that the substrate has a smooth surface.

The thickness of the organic film and the organic semiconductor layer of the organic thin film transistor of the present invention is not particularly limited. However, the thickness is determined such that the resultant film or layer is a uniform thin layer (i.e., the film or layer does not include gaps or holes adversely affecting the carrier transport property thereof). The thickness of the organic semiconductor layer is generally not greater than 1 μm, and preferably from 5 to 200 nm.

The organic thin film transistor of the present invention typically has configuration such that an organic semiconductor layer including the polymer of the present invention as a main component is formed therein while contacting the source electrode, drain electrode and insulating layer of the transistor.

Annealing

The organic film prepared above is typically annealed. Annealing is performed while the film is set on a substrate. The annealing temperature is determined depending on the property of the material constituting the substrate, but is preferably from room temperature to 300° C., and more preferably from 50 to 300° C. When the annealing temperature is too low, the organic solvent remaining in the organic film cannot be well removed therefrom. In contrast, when the annealing temperature is too high, the organic film tends to be thermally decomposed. Annealing is preferably performed in an oxygen, nitrogen, argon or air atmosphere. It is also preferable to perform annealing in an atmosphere including a gas of an organic solvent capable of dissolving the polymer because the molecular motion of the polymer is accelerated, and thereby a good organic thin film can be prepared. The annealing time is properly determined depending on the aggregation speed of the polymer.

Insulating Layer

An insulating layer is used for the organic thin film transistor of the present invention. Various insulating materials can be used for the insulating layer. Specific examples of the insulating materials include inorganic insulating materials such as silicon oxide, silicon nitride, aluminum oxide, aluminum nitride, titanium oxide, tantalum oxide, tin oxide, vanadium oxide, barium strontium titanate, barium zirconate titanate, lead zirconium titanate, lead lanthanum titanate, strontium titanate, barium titanate, barium magnesium fluoride, bismuth tantalate niobate, and trioxide yttrium; organic insulating materials such as polymer materials, e.g., polyimide, polyvinyl alcohol, polyvinyl phenol, polyester, polyethylene, polyphenylene sulfide, unsubstituted or halogen-atom substituted polyparaxylylene, polyacrylonitrile, and cyanoethylpullulan; etc. These materials can be used alone or in combination. Among these materials, materials having a high dielectric constant and a low conductivity are preferably used.

Suitable methods for forming such an insulating layer include dry processes such as CVD methods, plasma CVD methods, plasma polymerization methods, and vapor deposition methods; wet processes such as spray coating methods, spin coating methods, dip coating methods, inkjet coating methods, cast coating methods, blade coating methods, and bar coating methods; etc.

Modification of Interface Between Organic Semiconductor and Insulating Layer (Such as Hexamethylenedisilazane (HMDS))

In order to improve the adhesion between the insulating layer and organic semiconductor layer and to reduce the gate voltage and leak current, an organic thin film (intermediate layer) can be formed between the insulating layer and organic semiconductor layer. The materials for use in the intermediate layer are not particularly limited as long as the materials do not chemically affect the properties of the organic semiconductor layer, and for example, molecular films of organic materials, and thin films of polymers can be used therefor. Specific examples of the materials for use in preparing the molecular films include coupling agents such as octadecyltrichlorosilane, and hexamethyldisilazane (HMDS). Specific examples of the polymers for use in preparing the polymer films include the polymers mentioned above for use in the insulating layer. Such polymer films can serve as the insulating layer as well as the intermediate layer.

In addition, the organic thin film serving as the intermediate layer may be subjected to an anisotropic treatment such as rubbing.

Electrode

The materials of the electrodes (such as gate electrodes, source electrodes and drain electrodes) of the organic thin film transistor of the present invention are not particularly limited as long as the materials are electroconductive. Specific examples of the materials include metals such as platinum, gold, silver, nickel, chromium, copper, iron, tin, antimony, lead, tantalum, indium, aluminum, zinc, and magnesium; alloys of these metals; electroconductive metal oxides such as indium tin oxide; inorganic or organic semiconductors, whose electroconductivity is improved by doping or the like, such as silicon single crystal, polysilicon, amorphous silicon, germanium, graphite, polyacetylene, polyparaphenylene, polythiophene, polypyrrole, polyaniline, polythienylenevinylene, polyparaphenylenevinylene, and complexes of polyethylenedioxythiophene and polystyrene sulfonic acid.

It is preferable that the surface of the source electrode and drain electrode contacting the semiconductor layer has a lower electric resistance.

Specific examples of the method for forming the electrodes are the following:

(1) An electroconductive thin film of one or more of the materials mentioned above, which is prepared by a method such as vapor deposition or sputtering, is subjected to an electrode forming treatment using a known method such as photolithograph and lift-off methods to form an electrode;

(2) A resist pattern of electrode is formed on a foil of metal such as aluminum and copper using a thermal transfer method or an inkjet method, and the foil with the resist pattern is subjected to etching to form an electrode;

(3) A solution or dispersion of an electroconductive polymer, or dispersion of a particulate electroconductive material is sprayed using an inkjet method to form an electrode pattern of the electroconductive polymer or material;

(4) A coated film of an electroconductive material is subjected to a patterning treatment using a method such as lithography and laser abrasion methods to form an electrode; and (5) An ink or paste including an electroconductive polymer or a particulate electroconductive material is printed using a printing method such as relief printing, intaglio printing, planography, and screen printing, to form an electrode.

Extraction Electrode, and Protective Layer

Each of the electrodes of the organic thin-film transistor of the present invention can optionally have an extraction electrode.

The organic thin-film transistor of the present invention can stably operate in the air. However, in order to prevent the transistor from mechanically deteriorating, to protect the transistor from moisture and various gasses, and/or to protect the elements of the transistor from contacting each other or short-circuiting, a protective layer can be optionally formed, if desired.

Application of Organic Thin-Film Transistor

The organic thin-film transistor of the present invention can be used, for example, as an element for driving displays such as liquid crystal displays, organic electroluminescence displays and electrophoretic displays. In addition, the organic thin-film transistor of the present invention can also be used for electronic papers, which are integrated devices of these displays. Further, integrated circuits, in which the organic thin-film transistor of the present invention is integrated, can be used as devices such as IC tags.

FIGS. 1A-1D are schematic cross-sectional views illustrating examples of the organic thin film transistor of the present invention.

In FIGS. 1A-1D, numeral 1 denotes the organic semiconductor layer including the polymer of the present invention, and numerals 2, 3 and 4 respectively denote a source electrode, a drain electrode, and a gate electrode. Numeral 5 denotes a gate insulating layer.

Having generally described this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Example 1

Preparation of 2,6-bis(3-dodecylthiophene-2-yl)-benzo[1,2-d; 4,5-d']bisthiazole

The reaction formula is as follows.

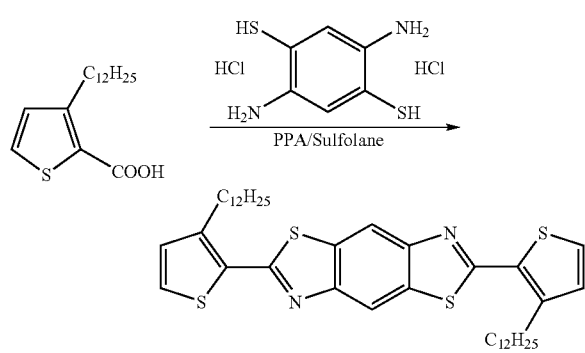

The following components were fed into a three-necked flask.

| | |
|---|---|
| 2,5-diamino-1,4-benzenethiol dihydrochlorides | 3.94 g |
| | (16.1 mM) |
| Polyphosphoric acid | 100 g |

The flask was repeatedly subjected to a decompression/argon-substitution treatment 5 times to remove the air therefrom. Next, the mixture was heated to 100° C. and agitated for 3 hours at 100° C. in an argon atmosphere.

On the other hand, 10.0 g (i.e., 33.8 mM or 2.1 eq) of 3-dodecyl-carboxyl-thiophene was dissolved in 100 ml of sulfolane to prepare a solution of the compound.

The thus prepared solution was added to the above-prepared mixture, and the mixture was further agitated for 1 hour at 100° C. in an argon atmosphere. Next, ion-exchange water was added to the mixture to form a precipitate, followed by filtering to obtain the precipitate. After the precipitate was subjected to silica-gel chromatography using 100% toluene as the solvent, followed by recrystallization using ethyl acetate. Thus, 10.6 g of 2,6-bis(3-dodecylthiophene-2-yl)-benzo[1,2-d; 4,5-d']-Bisthiazole was prepared. The yield was 95%. It was confirmed that the melting point of the compound is from 109 to 110° C.

The NMR Data of the Compound are as Follows.

$^1$H-NMR (CDCl$_3$, 400 MHz) δ 0.87 (t, 6H, J=8 Hz), 1.25-1.35 (m, 36H), 1.70-1.80 (q, 4H), 3.08 (t, 4H, J=8 Hz), 7.02 (d, 2H, J=8 Hz) 7.42 (d, 2H, J=8 Hz), 8.49 (s, 2H).

Preparation of 2,6-bis(3-dodecyl-5-iodothiophene-2-yl)-benzo[1,2-d; 4,5-d']bisthiazole and 2,6-bis(3-dodecyl-5-bromothiophene-2-yl)-benzo[1,2-d; 4,5-d']bisthiazole The reaction formula is as follows.

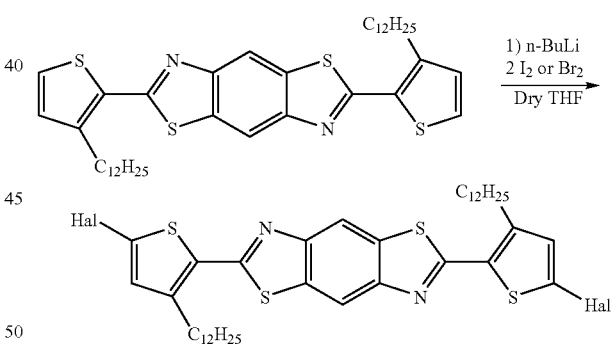

The following components were fed into a three-necked flask.

| | |
|---|---|
| 2,6-bis(3-dodecylthiophene-2-yl)-benzo[1,2-d;4,5-d']-bisthiazole prepared above | 460 mg |
| | (0.66 mM) |
| Tetrahydrofuran | 30 ml |

The mixture was cooled to −73° C. Next, 24 ml (i.e., 1.99 mM) of n-butyl lithium was dropped into the mixture. Two hours later, 230 mg (i.e., 2.5 eq) of iodine was added thereto. In addition, 30 minute later, 230 mg (i.e., 2.5 eq) of iodine was further added thereto. Two hours later, the temperature of the mixture was returned to room temperature. Next, the reaction product was subjected to an extraction treatment, column chromatography using a mixture solvent of hexane/ethyl acetate, and a recrystallization treatment. Thus, 440 mg of the diiodo compounds having the above-mentioned formula (wherein "Hal" represents I) was prepared. It was confirmed that the melting point of the diiodo compounds is from 119 to 121° C.

The NMR Data of the Diiodo Compound are as Follows.

$^1$H-NMR (CDCI$_3$, 400 MHz) δ0.87 (t, 6H, J=8 Hz), 1.26-1.47 (m, 36H), 1.72 (quint, 4H), 3.00 (t, 4H, J=8 Hz), 7.17 (s, 2H), 8.44 (s, 2H).

The above-mentioned procedure was repeated except that iodine was replaced with bromine to prepare the dibromo compounds (i.e., "Hal" represents Br in the above-mentioned formula). It was confirmed that the melting point of the dibromo compounds is from 117 to 119° C.

The NMR Data of the Dibromo Compound are as Follows.

$^1$H-NMR (CDCI$_3$, 400 MHz) δ0.87 (t, 6H, J=8 Hz), 1.26-1.47 (m, 36H), 1.72 (quint, 4H), 2.99 (t, 4H, J=8 Hz), 7.00 (s, 2H), 8.44 (s, 2H).

Synthesis of Polymer 1

Poly(2,6-bis(3-dodecyl-5-iodothiophene-2-yl)-benzo[1,2-d; 4,5-d']bisthiazole)

The reaction formula is as follows. The parenthetic unit is a repeat unit of a polymer.

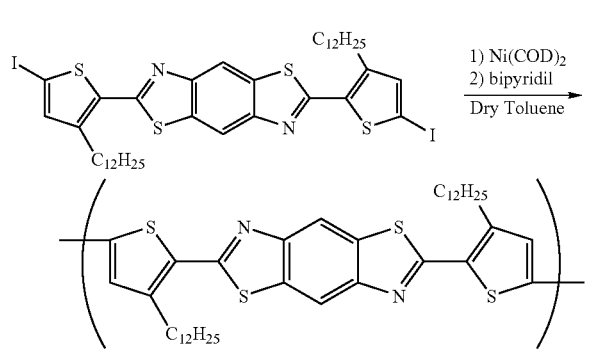

In a globe box, 127 mg (0.462 mM) of bis(1,5-cyclooctadiene)nickel (0) (i.e., Ni(COD)$_2$) was fed into a 50 ml three-necked flask, and then 12 ml of dehydrated toluene was added thereto. When a mixture of 72 mg of 2,2'-bipyridyl and 3 ml of toluene was added thereto, the color of the mixture changed from yellow to blue violet. Five minutes later, 350 mg (0.37 mM) of the above-prepared diiodo compound (having the formula at the left side of the reaction formula) was added thereto. The color rapidly changed to red brown. Next, the mixture was heated to 110° C. and agitated for 5.5 hours. After being cooled to room temperature, the reaction product was dispersed in 500 ml of ethanol to obtain a precipitate. The precipitate was subjected to Soxhlet extract using heptane for 12 hours to remove low molecular weight components, followed Soxhlet extract using methanol for 6 hours. Next, the reaction product was dissolved in 400 ml of chloroform, followed by filtering to remove chloroform-insoluble components therefrom. The chloroform solution was then washed repeatedly with ion-exchange water until the wash fluid had almost the same conductivity as ion-exchange water. After the washing operation, the chloroform solution was dropped into methanol to obtain a precipitate, followed by drying the precipitate. Thus, 84 mg of a polymer 1 of the present invention having the formula at the right side of the above-mentioned reaction formula and having a red-brown color was prepared.

Figure 2:
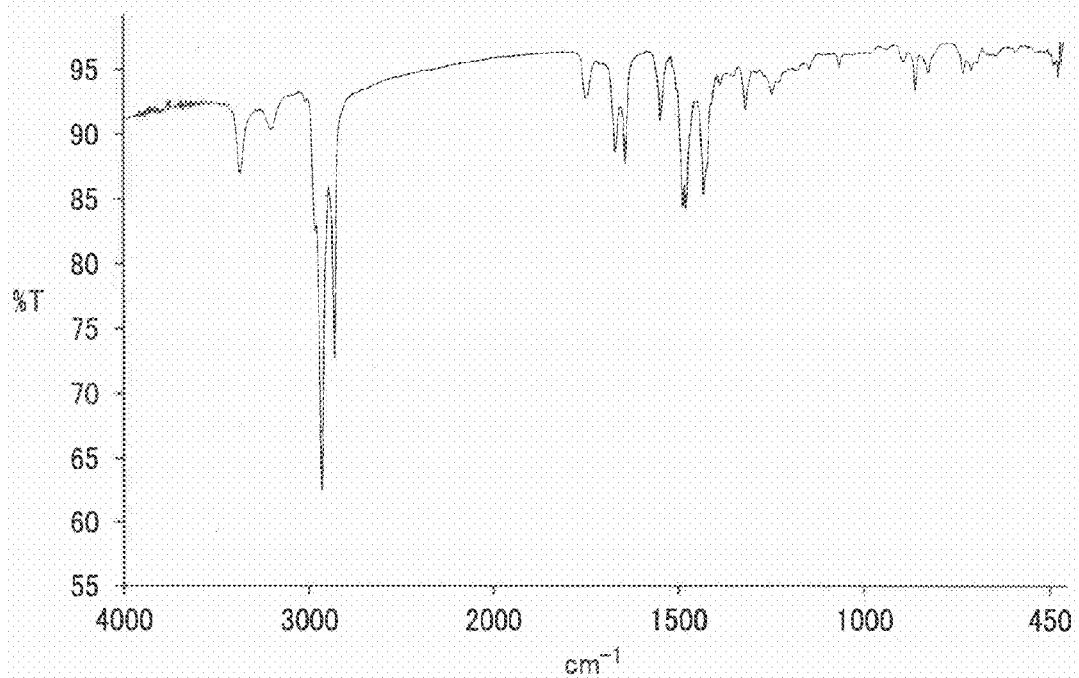
FIG. 2 is the IR spectrum of a first example of the benzobisthiazole polymer of the present invention.
Figure 3:
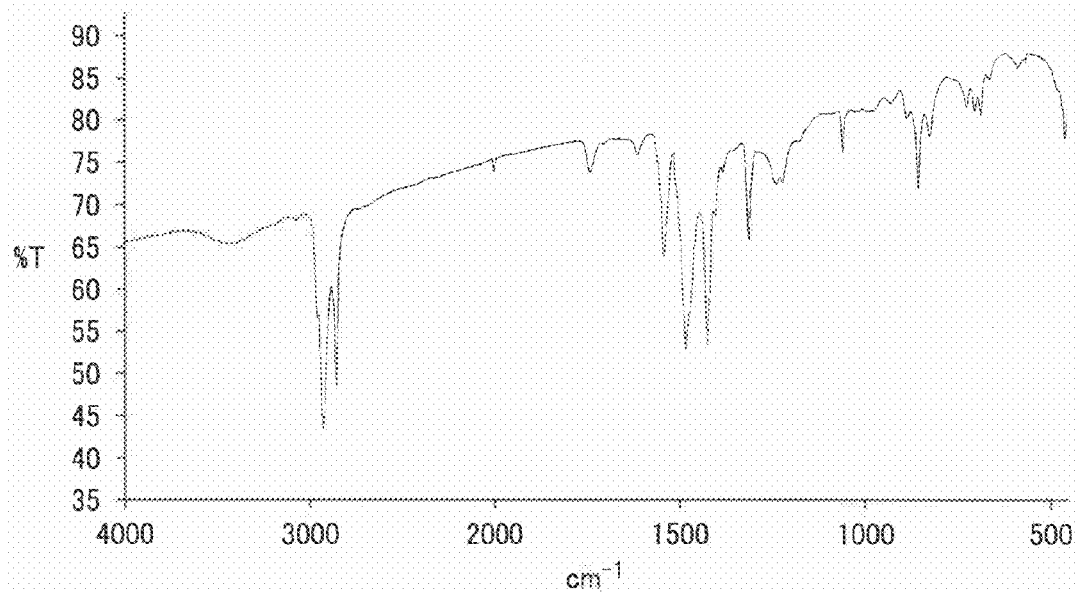
FIG. 3 is the IR spectrum of the first example of the polymer after the example is subjected to a heat treatment at 300° C.

It was confirmed that the polyethylene-conversion molecular weight of the polymer 1 determined by gel permeation chromatography is 5800 in number average molecular weight and 27000 in weight average molecular weight. The infrared absorption spectrum of the polymer 1 is illustrated in FIG. 2. In this case, a NaCl cast film of the polymer 1 was used for IR spectroscopy. In addition, the infrared absorption spectrum of the polymer 1, which was subjected to a heat treatment at 300° C., is illustrated in FIG. 3.

Example 2

Preparation of Benzobisthiazoleditrimethyltin Compound

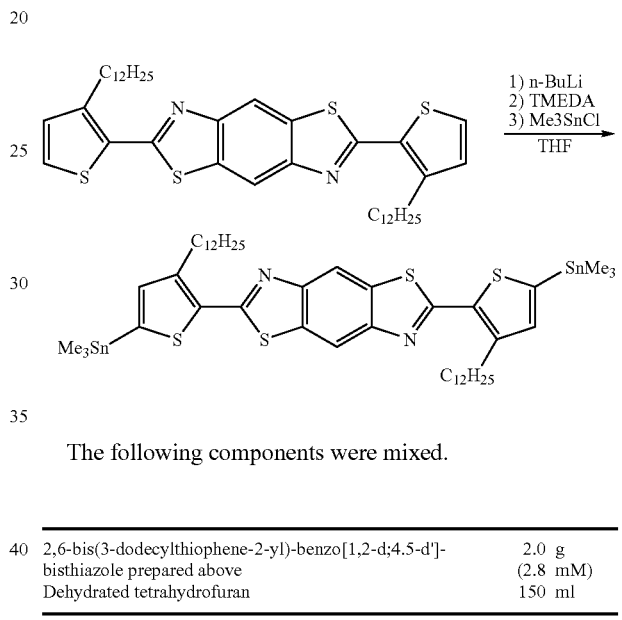

The following components were mixed.

| | |
|---|---|
| 2,6-bis(3-dodecylthiophene-2-yl)-benzo[1,2-d;4.5-d']-bisthiazole prepared above | 2.0 g (2.8 mM) |
| Dehydrated tetrahydrofuran | 150 ml |

The mixture was cooled to –73° C. Next, 0.94 ml (6.3 mM) of tetramethylenediamine was added to the mixture, and further 4.1 ml (6.3 mM) of n-butyl lithium was dropped into the mixture. After the mixture was agitated for 30 minutes at –73° C., the temperature of the mixture was increased to 10° C. After the mixture was cooled again to –73° C., 8.7 ml (8.7 mM) of a 1.0M hexane solution of trimethyltin chloride was added thereto. After the temperature of the mixture was increased to room temperature, the mixture was agitated for 1 hour. After the reaction product was subjected to an extraction treatment using ethyl acetate, followed by drying using magnesium sulfate, the reaction product was subjected to a separation/refinement treatment using a basic alumina column and a mixture solvent of hexane and toluene mixed in a ratio of 1/1, followed by a recrystallization treatment using hexane. Thus, 2.03 g of a yellow needle-form crystal was prepared. The yield was 69%. It was confirmed that the tin compound has a melting point of from 119 to 120.5° C.

The NMR Data of the Tin Compound are as Follows.

$^1$H-NMR (CDCI$_3$, 400 MHz) 0.42 (s, 18H), 0.88 (m, 6H), 1.26-1.55 (m, *H) 1.76 (quint, 4H, J=4 Hz), 3.07 (t, 4H, J=4 Hz), 7.08 (s, 2H), 8.47 (s, 2H).

Synthesis of Polymer 2

The reaction formula is as follows.

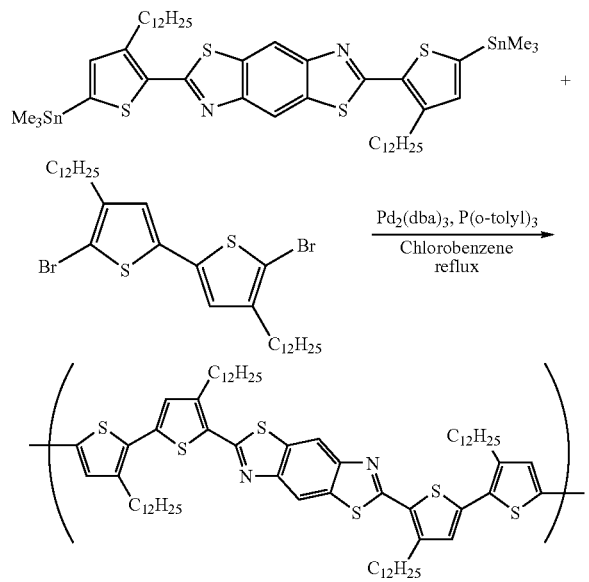

The following components were mixed in a three-necked flask containing a magnetic stirrer.

| | |
|---|---|
| Bithiophene dibromo compound | 660.7 mg |
| | (1.0 mM) |
| Above-prepared benzobisthiazoleditrimethyltin compound | 1018.8 mg |
| | (1.0 mM) |
| Dried chlorobenzene | 25.2 ml |
| (i.e., 15 ml × total weights (1.6795 g) of the compounds used) | |

The mixture was subjected to argon bubbling for 30 minutes.

Next, 18.3 mg (2 mol %) of $Pd_2(dba)_3$ and 24.3 mg (8 mol %) $P(o\text{-tolyl})_3$ were added thereto, and the mixture was further subjected to argon bubbling for 10 minutes. Further, the mixture was subjected to a heat/reflux treatment for 2.5 hours using an oil bath heated to 145° C. The reaction product was then dispersed in a mixture solvent including 1000 ml of methanol and 25 ml of hydrochloric acid, and the dispersion was agitated for 8 hours. After the dispersion was filtered, the reaction product was subjected to a Soxhlet extract using methanol for 5 hours, followed by a Soxhlet extract using hexane for 12 hours and another Soxhlet extract using chlorobenzene. The thus prepared condensed liquid was then dispersed in 1000 ml of methanol. Thus, 1.12 g of a brown-colored solid compound was obtained. The yield was 94%.

The thus-prepared compound was dissolved in tetrahydrofuran, followed by filtering using a filter having openings of 0.45 μm. When the molecular weight of the compound was determined by gel permeation chromatography (GPC), it was confirmed that the compound has a polystyrene-conversion number average molecular weight of greater than 4200 and a polystyrene-conversion weight average molecular weight of greater than 5300.

The IR spectrum of the thus synthesized compound obtained by using KBr is illustrated in FIG. 4.

Field Effect Transistor (FET) Evaluation

The surfaces of a p-doped silicon substrate with a length of 30 mm and a width of 30 mm were subjected to a thermal oxidation treatment to form an insulating layer (i.e., a $SiO_2$ layer) with a thickness of 200 nm on the both surfaces. One of the surfaces was covered with a resist film (i.e., TSMR8800 from Tokyo Ohka Kogyo Co., Ltd.) and the insulating layer (i.e., oxide film) of the other surface was removed using hydrofluoric acid. Next, an aluminum layer with a thickness of 300 nm was formed on the surface, from which the oxide film was removed, by a deposition method. Next, the resist film was removed using acetone. Thus, a substrate for an organic thin film transistor was prepared.

On the thus prepared substrate, organic thin film transistors were formed using the polymers prepared above.

Specifically, a 0.5% by weight solution of the polymer 1 was coated on the substrate by a spin coating method, followed by drying to form an organic semiconductor layer with a thickness of 30 nm on the substrate.

Next, gold was deposited thereon to form a source electrode and a drain electrode each having a thickness of 100 nm, wherein the channel length and width are 30 μm and 10 mm, respectively. Thus, an organic thin film transistor was prepared.

Figure 1D:
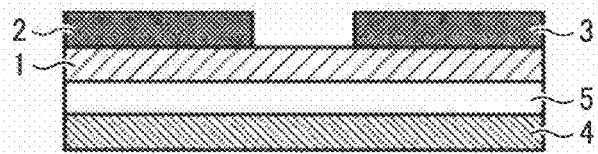

The thus prepared organic thin film transistor has the structure as illustrated in FIG. 1D, and the p-doped silicon substrate serving as the gate electrode 4 together with the thin aluminum layer formed on the lower surface of the silicon substrate.

The electron field-effect mobility (μ) of the organic thin film transistor was measured. The mobility (μ) was determined using the following equation:

$$Ids = \mu Cin W(Vg-Vth)^2/2L$$

wherein μ represents the electron field-effect mobility, Cin represents the capacitance of the gate insulating layer per a unit area, W represents the channel width, L represents the channel length, Vg represents the gate voltage, Ids represents the source drain current, and Vth represents the threshold voltage of the gate at which the channel starts to be formed.

Example 3

Figures 5A, 5B:
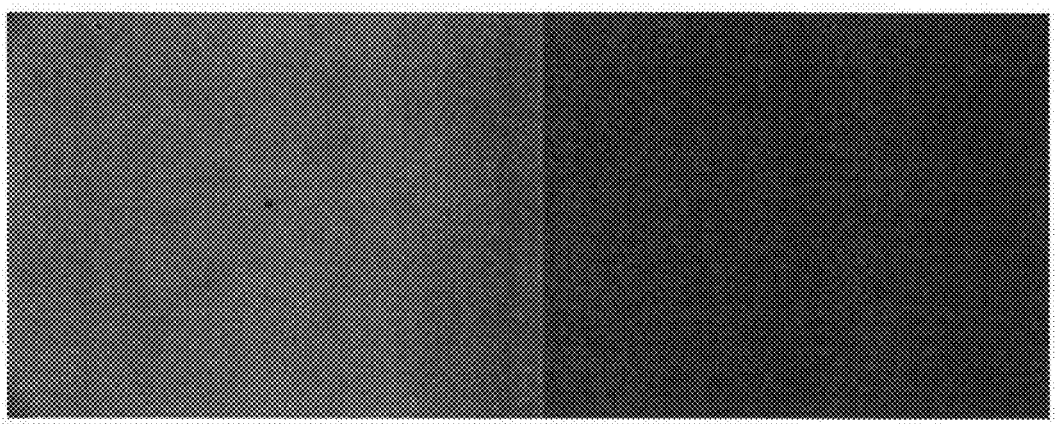
FIGS. 5A and 5B are photographs of an organic film obtained by naturally drying a solution of the first example of the benzobisthiazole polymer.

The coated layer of the polymer 1 formed on the silicon substrate was naturally dried for 12 hours in an argon atmosphere without performing a heat treatment (annealing treatment). The evaluation results of the organic thin film transistor of Example 2 are shown in Table 2. In addition, the surface of the organic thin film was observed with a polarization microscope with 400 power magnification, and the photograph is shown in FIGS. 5A and 5B. FIGS. 5A and 5B are a photograph taken in an open nichol manner, and a photograph taken in a cross nichol manner. It is clear from FIGS. 5A and 5B that the polymer has a good film forming property.

Example 4

The procedure for preparation of the organic thin film transistor in Example 3 was repeated except that the coated layer of the polymer formed on the substrate was subjected to an annealing treatment (heat treatment) in which the substrate is heated for 1 hour on a hot plate heated to 80° C. in an argon atmosphere. The evaluation results of the organic thin film transistor of Example 4 are also shown in Table 2.

Example 5

Figures 6A, 6B:
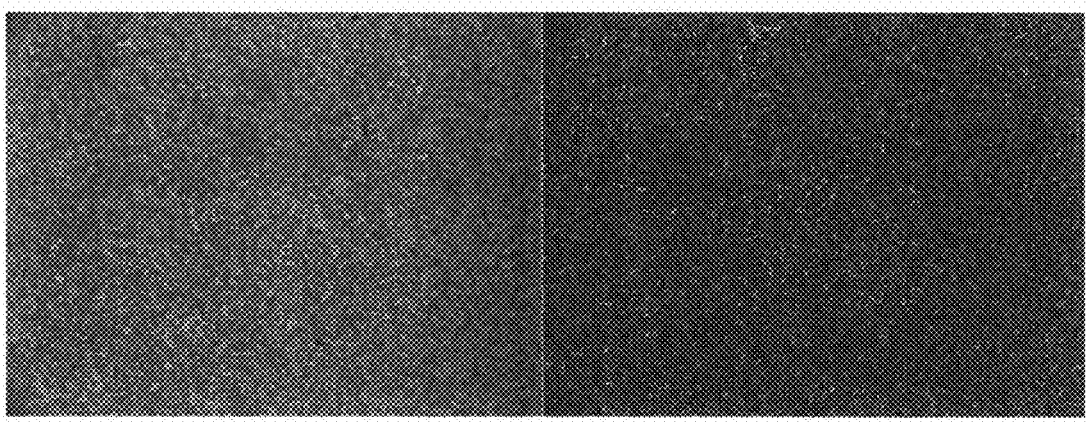
FIGS. 6A and 6B are photographs of an organic film obtained by drying a solution of the first example of the benzobisthiazole polymer, followed by annealing at 175° C.

The procedure for preparation of the organic thin film transistor in Example 3 was repeated except that the coated layer of the polymer formed on the substrate was subjected to an annealing treatment (heat treatment) in which the substrate is heated for 1 hour on a hot plate heated to 175° C. in an argon atmosphere. In addition, the surface of the organic thin film was observed with a polarization microscope, and the photograph is shown in FIG. 6. FIGS. 6A and 6B are a photograph with a parallel nichol, and a photograph with a cross nichol. It is clear from FIGS. 6A and 6B that by performing an annealing treatment, the film has an ordered structure due to the stereoregularity of the polymer.

Example 6

Figure 7:
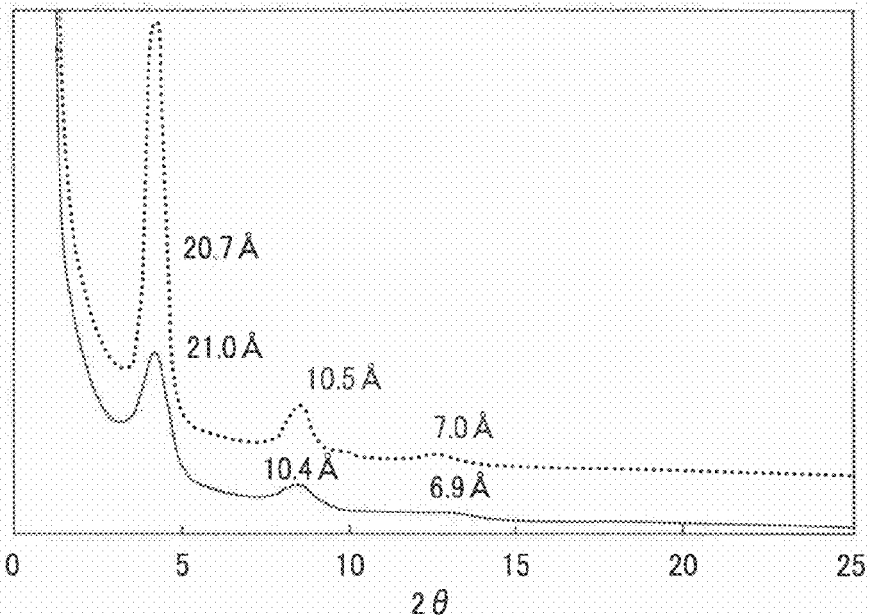
FIG. 7 is an X-ray out-of-plane diffraction spectrum of an organic film of a second example of the benzobisthiazole polymer.

The procedure for preparation of the organic thin film transistor in Example 3 was repeated except that the polymer 1 was replaced with the polymer 2. The X-ray out-of-plane diffraction spectrum of the organic film is shown in FIG. 7 using a solid line. It is clear from the spectrum that the organic film has high stereoregularity.

Example 7

Figure 8:
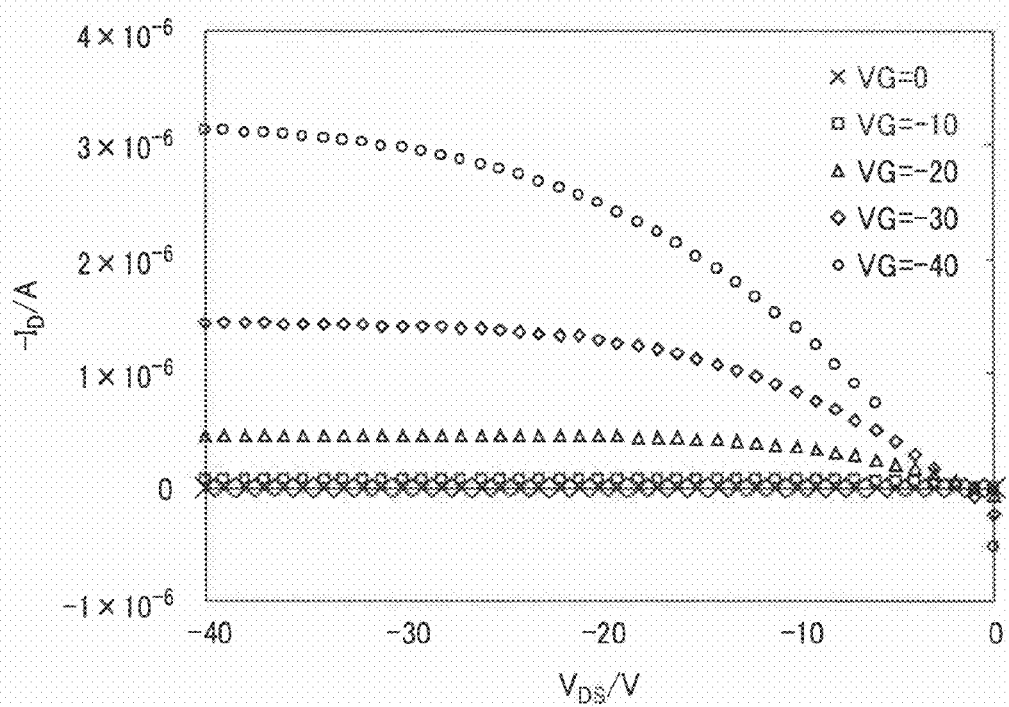
FIG. 8 illustrates the output characteristics of an organic thin film transistor prepared by using the second example of the benzobisthiazole polymer.

The procedure for preparation of the organic thin film transistor in Example 6 was repeated except that the coated layer of the polymer 2 formed on the substrate was subjected to an annealing treatment (heat treatment) in which the substrate is heated for 1 hour on a hot plate heated to 175° C. in an argon atmosphere. The X-ray out-of-plane diffraction spectrum of the organic film is shown in FIG. 7 using a dotted line. It is clear from the spectrum that the organic film has a high stereoregularity. It is clear from the spectrum that the organic film has higher stereoregularity than the organic film of Example 6. In addition, the output characteristics of the organic thin film transistor using this organic film is illustrated in FIG. 8.

Comparative Example 1

The polymer having the following formula was synthesized by reference to Chem. Mater. 2004, 16, 4286-4291, and Macromolecules, 1996, 29, 3787-3792.

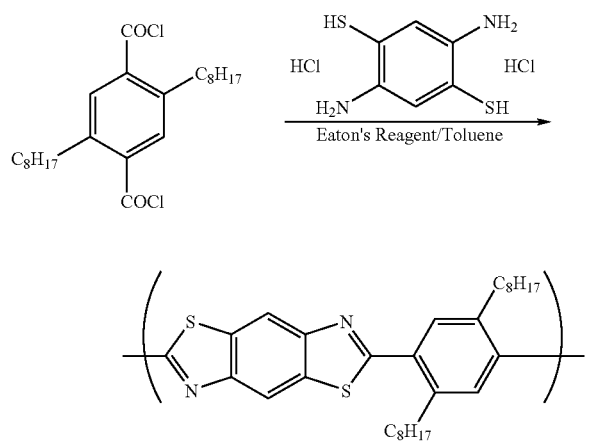

The thus prepared polymer was evaluated by the same method as mentioned above in Example 3.

The evaluation results of the organic thin film transistors of Examples 3-7 and Comparative Example 1 are shown in Table 2.

TABLE 2

| | Annealing temperature | Mobility (μ) | ON/OFF ratio |
|---|---|---|---|
| Example 3 | Naturally dried | $6.1 \times 10^{-4}$ | $10^5$ |
| Example 4 | 80° C. | $1.0 \times 10^{-3}$ | $10^5$ |
| Example 5 | 175° C. | $8.1 \times 10^{-3}$ | $10^6$ |
| Example 6 | Naturally dried | $2.5 \times 10^{-3}$ | $10^6$ |

TABLE 2-continued

| | Annealing temperature | Mobility (μ) | ON/OFF ratio |
|---|---|---|---|
| Example 7 | 175° C. | $6.7 \times 10^{-2}$ | $10^6$ |
| Comparative Example 1 | 80° C. | Not observed | Not observed |

Oxidative Stability Test

Example 8

In order to evaluate the oxidative stability of the polymer 1, a thin film of the polymer 1 was prepared. The ionization potential (Ip) of the polymer was measured with an atmospheric ultraviolet photoelectron counting (a-UPC) instrument AC-2 from Riken Keiki Co., Ltd., and cyclic voltammetry (CV). Specifically, a graph showing the relationship between energy of ultraviolet light and square root of counts of photoelectrons (Yield) was prepared. An approximated line was drawn in the graph using a least square method to determine the threshold energy of photoelectron emission. The results are shown in Table 3.

In addition, an oxidative stability test in which the filed effect mobility of the thin film is measured in an argon atmosphere and the film is then allowed to settle for 1 week in the air while shielding light to measure again the filed effect mobility of the thin film was performed. The oxidative stability is evaluated as follows.
○: The ON current (Ion) and mobility of the film are decreased by less than 50%.
X: The ON current (Ion) and mobility of the film are decreased by not less than 50%.
The results are also shown in Table 3.

Example 9

The procedure for evaluation in Example 8 was repeated except that the polymer 1 was replaced with the polymer 2.
The results are shown in Table 3.

Comparative Example 2

The procedure for evaluation in Example 8 was repeated except that the polymer 1 was replaced with a typical thiophene compound rr-P3HT (from Sigma Aldrich Corp.).
The results are shown in Table 3.

TABLE 3

| | Polymer | Ip (eV) | Oxidative stability test |
|---|---|---|---|
| Ex. 8 | Polymer 1 | 5.4 | ○ |
| Ex. 9 | Polymer 2 | 5.1 | ○ |
| Comp. Ex. 2 | P3HT | 4.7 | X |

It is clear from Tables 2 and 3 that the polymer of the present invention and the organic thin film transistor using the polymer, which have the 2-thienobenzo[1,2-d; 4,5-d']bisthiazole skeleton having a high oxidation potential, have not only good oxidative stability but also a high mobility and a high ON/OFF ratio due to the extended π-conjugated system. In addition, it is clear from the X-ray out-of diffraction spectra that the organic film of the present invention has high stereoregularity and the stereoregularity is further enhanced by annealing the organic film.

Next, the benzobisthiazole compound of the present invention will be explained.

Benzobisthiazole tin compounds having the following formula (3) (i.e., benzobisthiazole skeleton) can also be preferably used as electroluminescence materials, organic semiconductor materials and charge transport materials or intermediate materials thereof.

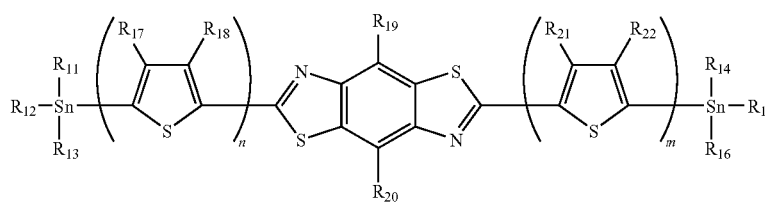

(3)

wherein each of $R_{11}$ to $R_{22}$ represents a hydrogen atom, a halogen atom, a substituted or unsubstituted alkyl group, a substituted or unsubstituted alkoxyl group, or a substituted or unsubstituted alkylthio group; and each of m and n is 0 or a positive integer, wherein when m is 2 or more, each of $R_{21}$ may be the same as or different from the others, and each of $R_{22}$ may be the same as or different from the others, and wherein when n is 2 or more, each of $R_{17}$ may be the same as or different from the others, and each of $R_{18}$ may be the same as or different from the others.

As mentioned below, such tin compounds can be prepared at a high reaction speed and a high yield. Therefore, electroluminescence materials, organic semiconductor materials and charge transport materials can be prepared at a high process yield. In addition, when polymers of such tin compounds are prepared, the polymerization degree and polydispersity can be controlled, and thereby the desired materials can be stably prepared.

When the groups $R_{11}$ to $R_{22}$ are substituted or unsubstituted alkyl groups, linear, branched or cyclic alkyl groups having 1 to 25 carbon atoms are preferable. These alkyl groups can further include a fluorine atom, a cyano group, or a phenyl group, which is optionally substituted with a halogen atom or a linear or branched alkyl group. Specific examples thereof include methyl, ethyl, n-propyl, i-propyl, t-butyl, s-butyl, n-butyl, pentyl, hexyl, heptyl, octyl, nonyl, decyl, 3,7-dimethyloctyl, 2-ethylhexyl, trifluoromethyl, 2-cyanoethyl, benzyl, 4-chlorobenzyl, 4-methylbenzyl, cyclopentyl, and cyclohexyl groups.

Specific examples of the alkoxyl and alkylthio groups for use as the groups $R_{11}$ to $R_{22}$ include alkoxyl and alkylthio groups in which an oxygen or sulfur atom is incorporated in a binding position of the above-mentioned alkyl groups.

When the groups $R_{11}$ to $R_{22}$ are halogen atoms, fluorine, chlorine and bromine atoms are preferable.

In formula (3), each of m and n is 0 or a positive integer (an integer of not less than 1), and is preferably from 0 to 3.

Among these tin compounds having formula (3), compounds having the following formula (4) having an axisymmetric or plane-symmetric skeleton are preferable.

wherein $R_{23}$ represents a linear or branched alkyl group; each of $R_{24}$ to $R_{26}$ represents a hydrogen atom, a halogen atom, a substituted or unsubstituted alkyl group, a substituted or unsubstituted alkoxyl group, or a substituted or unsubstituted alkylthio group; p is 0 or a positive integer, wherein when p is 2 or more, each of $R_{24}$ is the same as or different from the others, and each of $R_{25}$ is the same as or different from the others.

Compounds having a symmetric skeleton have advantages over compounds having an asymmetric skeleton such that the number of processes of preparing the compounds is smaller than that in the case of asymmetric compounds, and the refining process can be easily performed due to high crystallinity of the compounds. In addition, when the compounds are used as intermediates of polymers, the resultant polymers tend to have a high crystallinity, i.e., charge transport materials or organic semiconductor materials having good physical properties (such as high carrier transportability) can be provided.

The above-mentioned substituted or unsubstituted alkyl groups for use as $R_{11}$ to $R_{22}$ in formula (3) can also be used for $R_{23}$. In addition, the above-mentioned halogen atoms, substituted or unsubstituted alkyl groups, alkoxyl groups and alkylthio groups for use as $R_{11}$ to $R_{22}$ can also be used for $R_{24}$ to $R_{26}$. Further, p is the same as m or n in formula (3) and preferably from 0 to 3.

It is preferable that $R_{11}$ to $R_{13}$, $R_{14}$ to $R_{16}$, and $R_{23}$ in formula (3) and (4) are a n-butyl group or a methyl group because general reagents such as trimethyltin chloride and tributyltin chloride can be used for preparing the compounds (i.e., raw materials therefor can be easily obtained).

Tin compounds having formula (3) or (4) can be prepared, for example, by the following method.

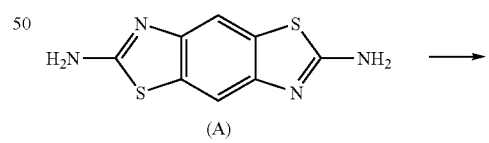

(A)

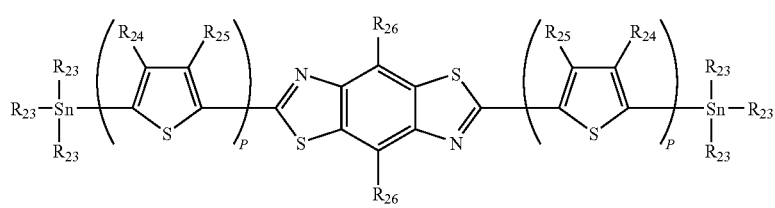

(4)

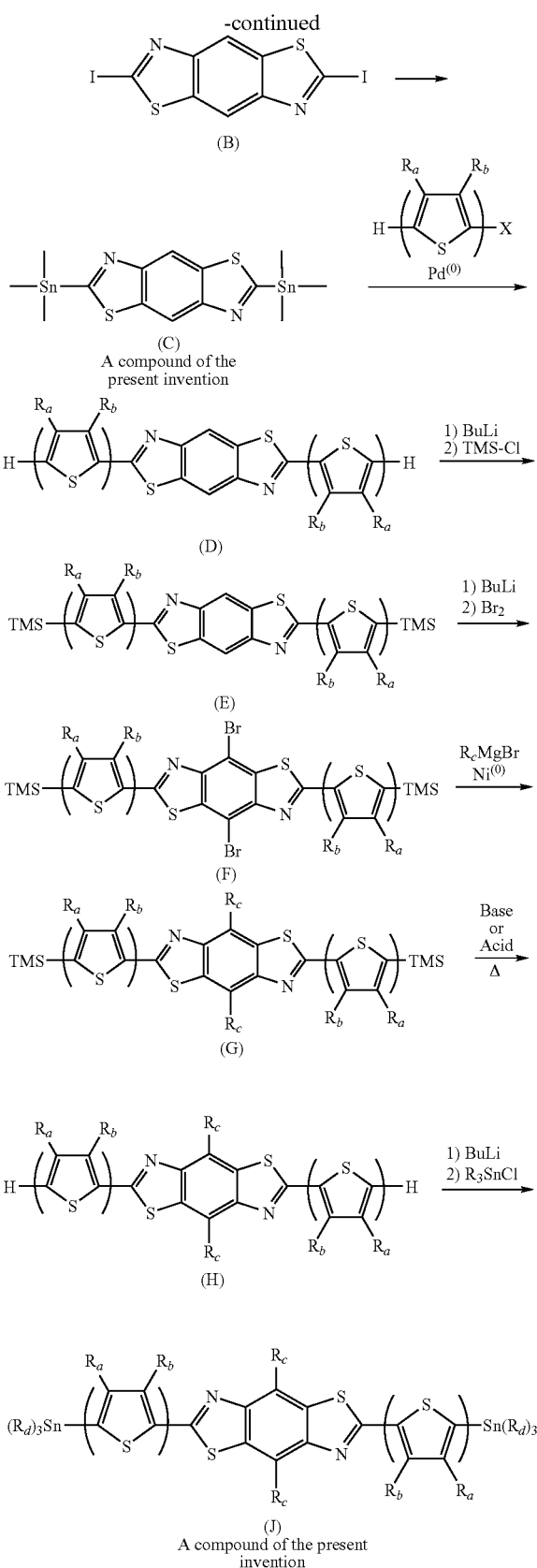

(B)

(C) A compound of the present invention (D)

(E)

(F)

(G)

(H)

(J) A compound of the present invention

The compound having the above-mentioned formula (A) is disclosed in Macromolecules, 1981, 14, 915. For example, the compound (A) is reacted with tert-butyl nitrite in the presence of iodine to be diazotized and then iodinated, i.e., to prepare a compound having the above-mentioned formula (B). In addition, for example, the compound (B) is reacted with a lithium compound such as alkyllithium to be lithiated, followed by a reaction with trialkylhalide to prepare a compound having the above-mentioned formula (C). Specific examples of the alkyllithium compounds include n-butyl lithium, sec-butyl lithium and tert-butyl lithium. The compound (C) is an example of the compound of the present invention having formula (3) or (4) in which m, n and p is 0.

The compound (C) can be easily converted to a compound having the above-mentioned formula (D) using the Stille reaction described in Strategic Applications of Named reactions In Organic Synthesis. Alternatively, the compound (D) can be prepared by a method, in which a 2-carboxythiophene derivative and 2,5-diamino-1,4-benzenethiol dihydrochloride are subjected to a condensation reaction. Specifically, as disclosed in Chem. Mater. 2004, 16, 4286-4291, a 2-carboxythiophene derivative is converted to an acid chloride using thionyl chloride, followed by polymerization using an Eaton's reagent. Alternatively, as disclosed in Macromolecules, 1996, 29, 3787-3792, the compound (D) can be prepared by subjecting a polyphosphoric acid (PPA) and sulfolane to a condensation reaction.

In the above-mentioned reaction formula in which the compound (C) is converted to the compound (D), the group X represents a group selected from chlorine atom, bromine atom, iodine atom, trifluoromethanesulfonate group (OTf), and phosphonic acid ester groups (OPO(OR)$_2$), and is preferably an iodine atom or a bromine atom.

A compound having the above-mentioned formula (E) is prepared, for example, by lithiating the 5- and 5'-position of the thiophene ring, and then reacting the reaction product with trimethylsilyl chloride (TMS).

A compound having the above-mentioned formula (F) is prepared, for example, by metalizing the 4- and 8-positions of benzobisthiazole and then treating the reaction product with an electrophilic agent. Specific examples of the metalizing agents include alkyl lithium, lithium amide, and lithium-zinc ate complexes. Specific examples of the alkyl lithium compounds include n-butyl lithium, sec-butyl lithium, and tert-butyl lithium. Specific examples of the lithium amide compounds include lithium diisopropyl amide, lithium diethyl amide, and lithium tetramethyl piperidide (LiTMP). Specific examples of the electrophilic agents include chlorine, bromine and iodine, and bromine and iodine are preferably used.

A compound having the above-mentioned formula (G) is prepared, for example, by reacting the compound (F) with a Grignard reagent in the presence of a metal catalyst.

A compound having the above-mentioned formula (H) is prepared, for example, by removing the trimethylsilyl groups from the compound (G) in the presence of an acid or alkali, resulting in conversion of the groups to protons.

A compound having the above-mentioned formula (J) is prepared, for example, by lithiating the 5- and 5'-position of the thiophene ring, followed by reaction with trimethyltin chloride.

Thus, the benzobisthaizole tin compound of the present invention is prepared.

Specific examples of the benzobisthaizole tin compound of the present invention include compounds having the following formulae.

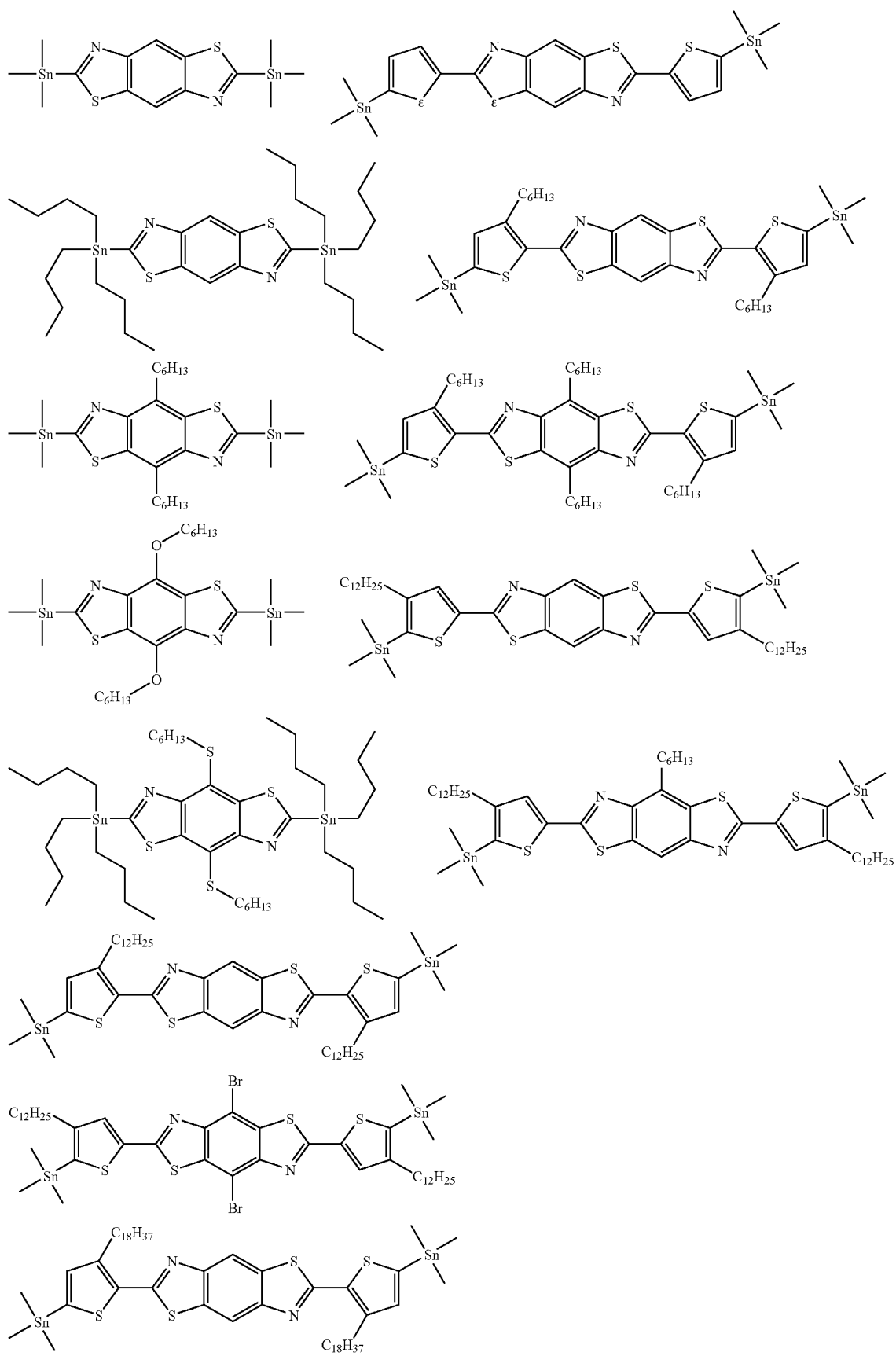

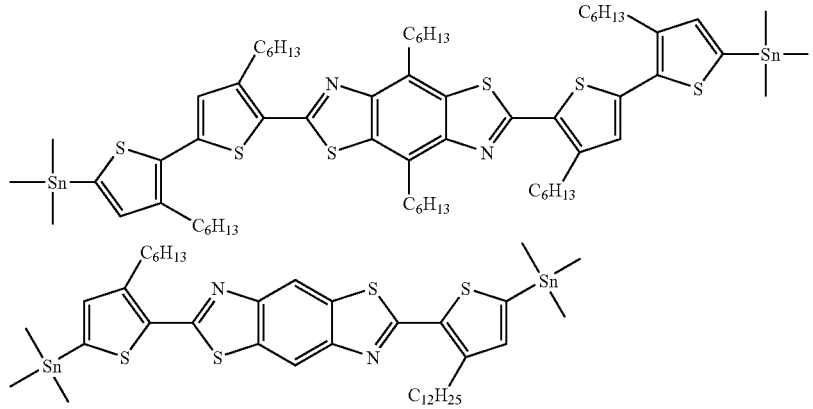

The benzobisthiazole tin compound of the present invention can also be used as intermediates, and π-conjugated materials can be easily prepared, for example, by using the Stille reaction described in Strategic Applications of Named reactions In Organic Synthesis as illustrated by the following reaction formulae.

and tolyl groups), heteroaryl groups, acyl groups (such as acetyl, acetoimidoyl, and thioacetyl groups), and thienyl groups. The group $Ar_2$ is a divalent group obtained from the groups mentioned above for use as the group $Ar_1$.

By subjecting an organic tin compound and an organic electrophilic reacting agent to the Stille reaction, a C-C sigma

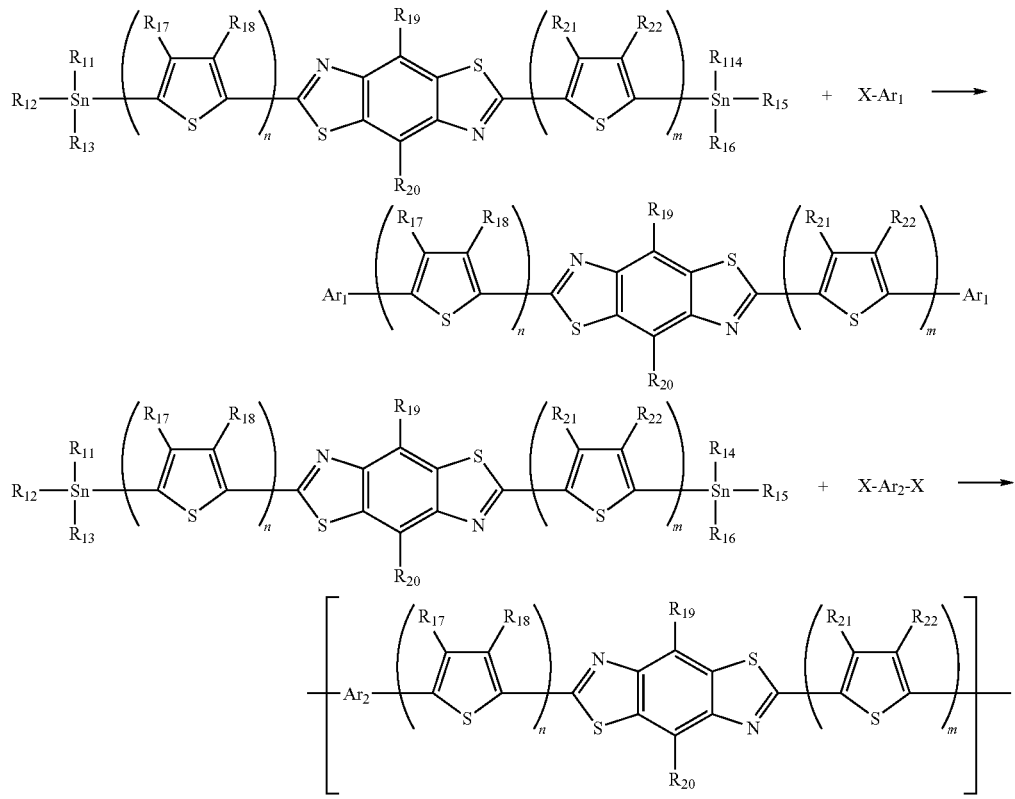

Specific examples of the group X of the compound used for the above-mentioned reactions include chlorine atom, bromine atom, iodine atom, trifluoromethanesulfonate group (OTf), and phosphonic acid ester groups ($OPO(OR)_2$). Among these groups, an iodine atom or a bromine atom is preferable. Specific examples of the group $Ar_1$ of the compound used for the above-mentioned reactions include alkenyl groups (such as vinyl group), aryl groups (such as phenyl bond can be formed. In this reaction, a metal catalyst, i.e., a zerovalent palladium catalyst, is preferably used.

Specific examples of such palladium catalysts include palladium bromide, palladium chloride, palladium iodide, palladium cyanide, palladium acetate, palladium trifluoroacetate, palladium acetylacetonate ($Pd(acac)_2$), diacetatebis(triphenylphosphine)palladium ($Pd(OAc)_2(PPh_3)_2$), tetrakis(triphenylphosphine)palladium ($Pd(PPh_3)_4$), dichlorobis (acetonitrile)palladium (Pd(CH$_3$CN)$_2$Cl$_2$), dichlorbis (benzonitrile)palladium (Pd(PhCN)$_2$Cl$_2$), dichloro[1,2-bis(diphenylphosphino)ethane]palladium (Pd(dppe) Cl$_2$), dichloro[1,1-bis(diphenylphosphino)ferrocene]palladium (Pd(dppf)Cl$_2$), dichlorobis(tricyclohexylphosphine)palladium (Pd[P(C$_6$H$_{11}$)$_3$]$_2$Cl$_2$), dichlorobis(triphenylphosphine)palladium (Pd(PPh$_3$)$_2$Cl$_2$), tris(dibenzylideneacetone)dipalladium (Pd$_2$(dba)$_3$), and bis(dibenzylideneacetone)palladium (Pd (dba)$_2$), etc. Among these catalyste, phosphine catalysts such as tetrakis(triphenylphosphine)palladium (Pd (PPh$_3$)$_4$), dichloro[1,2-bis(diphenylphosphino)ethane]palladium (Pd(dppe)Cl$_2$), and dichlorobis(triphenylphosphine)palladium (Pd(PPh$_3$)$_2$Cl$_2$) are preferably used.

In addition, palladium catalysts, which are synthesized in a reaction system by a reaction of a palladium complex with a ligand, can also be used as palladium catalysts. Specific examples of the ligands include triphenylphosphine, trimethylphosphine, triethylphosphine, tris(n-butyl)phosphine, tris(tert-butyl)phosphine, tris(tert-butyl)methylphosphine, tris(i-propyl)phosphine, tricyclohexylphosphine, tris(o-tolyl)phosphine, tris(2-furyl)phosphine, 2-dicyclohexylphosphinobiphenyl, 2-dicyclohexylphosphino-2'-methylbiphenyl, 2-dicyclohexylphosphino-2',4',6'-triisopropyl-1,1'-biphenyl, 2-dicyclohexylphosphino-2',6'-dimethoxy-1,1'-biphenyl, 2-dicyclohexylphosphino-2'-(N,N'-dimethylamino)biphenyl, 2-diphenylphosphino-2'-(N,N'-dimethylamino)biphenyl, 2-(di-tert-butyl)phosphino-2'-(N,N'-dimethylamino)biphenyl, 2-(di-tert-butyl)phosphinobiphenyl, 2-(di-tert-butyl)phosphino-2'-methylbiphenyl, diphenylphosphinoethane, diphenylphosphinopropane, diphenylphosphinobutane, diphenylphosphinoethylene, diphenylphosphinoferrocene, ethylene diamine, N,N',N'',N'''-tetramethylethylene diamine, 2,2'-bipyridyl, 1,3-diphenyldihydroimidazolylidene, 1,3-dimethyldihydroimidazolylidene, diethyldihydroimidazolylidene, 1,3-bis(2,4,6-trimethylphenyl)dihydroimidazolylidene, and 1,3-bis(2,6-diisopropylphenyl)dihydroimidazolylidene.

Palladium catalysts having such a ligand can be used as cross-coupling catalysts.

Other metal catalysts such as manganese catalysts, nickel catalysts, and copper catalysts can also be used.

The solvent used for the coupling reaction is not particularly limited as long as the solvent does not affect the coupling reaction. Specific examples of the solvents include aromatic hydrocarbons such as toluene, xylene and benzene; esters such as methyl acetate, ethyl acetate, and butyl acetate; ethers such as diethyl ether, tetrahydrofuran, dioxane, dimethoxyethane, and diisopropyl ether; amines such as triethyl amine, and diethyl amine; halogenated hydrocarbons such as methyl chloride, chloroform, dichloromethane, dichloroethane, dibromoethane, and dichlorobenzene; ketones such as acetone, and methyl ethyl ketone; amides such as dimethylformamide, and dimethylacetamide; nitrites such as acetonitrile; dimethylsulfoxide, etc. These solvents can be used alone or in combination. It is preferable that the solvent is dried and deaerated before use.

The above-mentioned reaction is preferably performed at a temperature of from 0 to 200° C., more preferably from 20 to 150° C., and even more preferably from 50 to 100° C. When the reaction temperature is too high, the reaction cannot be controlled. In contrast, when the reaction temperature is too low, the reaction speed is slow.

The reaction time, which is determined depending on factors such as reaction temperature, properties of the compounds to be reacted, and properties of metal catalysts used for the reaction, is generally from 1 minute to 24 hours, and preferably from 10 minutes to 12 hours.

Example 10

Synthesis of 2,6-bis(3-dodecylthiophene-2-yl)-benzo[1,2-d; 4-5-d']bisthiazole

The reaction formula is as follows.

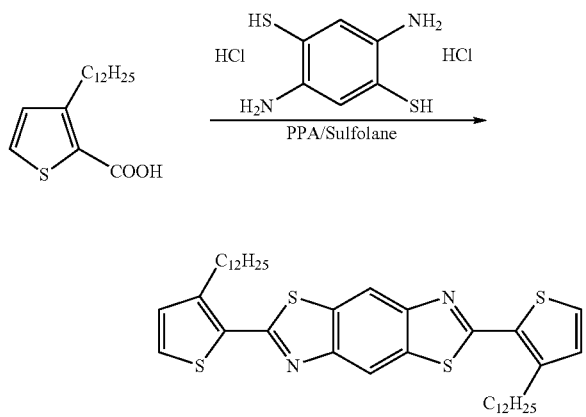

The following components were fed into a three-neck flask.

| | |
|---|---|
| 2,5-diamino-1,4-benzenethiol dihydrochlorides | 3.94 g (16.1 mM) |
| Polyphosphoric acid | 100 g |

The flask was repeatedly subjected to a decompression/argon-substitution treatment 5 times to remove the air therefrom. Next, the mixture was heated to 100° C. and agitated for 3 hours at 100° C. in an argon atmosphere.

On the other hand, 10.0 g (i.e., 33.8 mM or 2.1 eq) of 3-dodecyl-carboxyl-thiophene was dissolved in 100 ml of sulfolane to prepare a solution of the compound.

The thus prepared solution was added to the above-prepared mixture, and the mixture was further agitated for 1 hour at 100° C. in an argon atmosphere. Next, ion-exchange water was added to the mixture to form a precipitate, followed by filtering to obtain the precipitate. After the precipitate was subjected to silica-gel chromatography using 100% toluene as the solvent, followed by recrystallization using ethyl acetate. Thus, 10.6 g of 2,6-bis(3-dodecylthiophene-2-yl)-benzo[1,2-d; 4,5-d']-Bisthiazole was prepared. The yield was 95%. It was confirmed that the melting point of the compound is from 109 to 110° C.

The NMR Data of the Compound are as Follows.

$^1$H-NMR (CDCl$_3$, 400 MHz) δ 0.87 (t, 6H, J=8 Hz), 1.25-1.35 (m, 36H), 1.70-1.80 (q, 4H), 3.08 (t, 4H, J=8 Hz), 7.02 (d, 2H, J=8 Hz) 7.42 (d, 2H, J=8 Hz), 8.49 (s, 2H).

Synthesis of Benzobisthiazole Trimethyltin

The reaction formula is as follows.

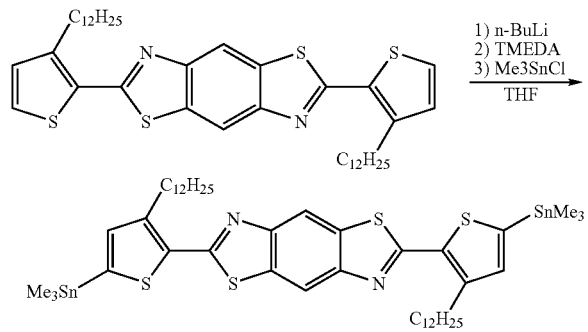

At first, 2.0 g (2.8 mM) of the above-prepared 2,6-bis(3-dodecylthiophene-2-yl)-benzo[1,2-d; 4,5-d']-bisthiazole was mixed with 150 ml of dehydrated tetrahydrofuran, and the mixture was cooled to −73° C. After 0.94 ml (6.3 mM) of tetramethylenediamine (TMEDA) was added thereto, 4.1 ml (6.3 mM) of n-butyl lithium was dropped to the mixture. After the mixture was agitated for 30 minutes at the temperature (−73° C.), the temperature of the mixture was raised to 10° C. After the mixture was cooled again to −73° C., 8.7 ml (8.7 mM) of a 1.0M hexane solution of trimethyltin chloride was dropped to the mixture. After the temperature of the mixture was raised to room temperature, the mixture was agitated for 1 hour. The reaction product was extracted using ethyl acetate, followed by drying using magnesium sulfate, and separation and refinement using a basic alumina column using a mixture solvent of hexane and toluene mixed in a ratio of 1/1. The thus refined reaction product was then recrystallized. Thus, a yellow needle-form crystal was obtained. The weight of the compound (yellow needle-form crystal) was 2.03 g and the yield was 69%. It was confirmed that the compound has a melting point of from 119.0 to 120.5° C.

The NMR Data of the Compound are as Follows.

$^1$H-NMR (CDCl$_3$, 400 MHz) 0.42 (s, 18H), 0.88 (m, 6H), 1.26-1.55 (m, *H), 1.76 (quint, 4H, J=4 Hz), 3.07 (t, 4H, J=4 Hz), 7.08 (s, 2H), 8.47 (s, 2H).

Figure 9:
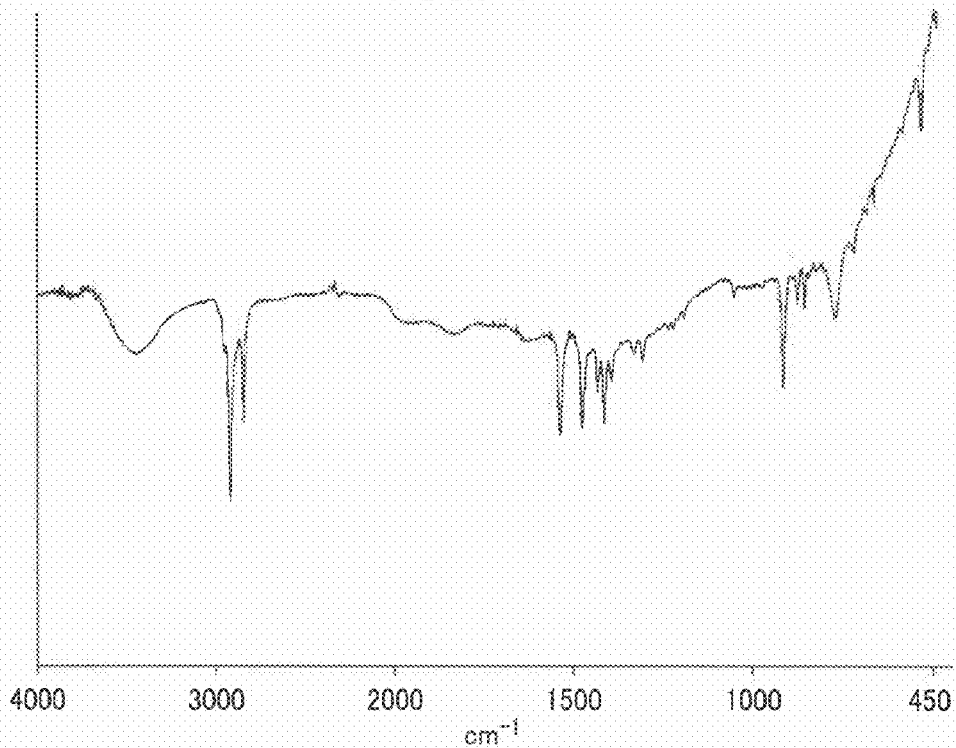
FIG. 9 is the IR spectrum of an example of the benzobisthiazole compound of the present invention.

The IR spectrum of the compound obtained by using KBr is shown in FIG. 9.

In order to show the superiority of the compound of the present invention, a polymer of the present invention was synthesized from the above-prepared tin compound using a Stille reaction, and the polymer was synthesized from a boron compound having a benzothiazole skeleton using a Suzuki coupling reaction to be compared with the polymer synthesized from the above-prepared tin compound.

Application Example 1

The reaction formula is as follows.

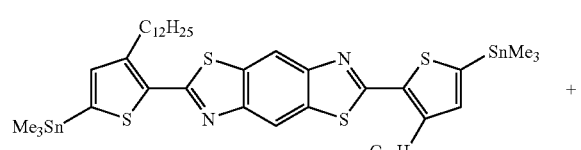

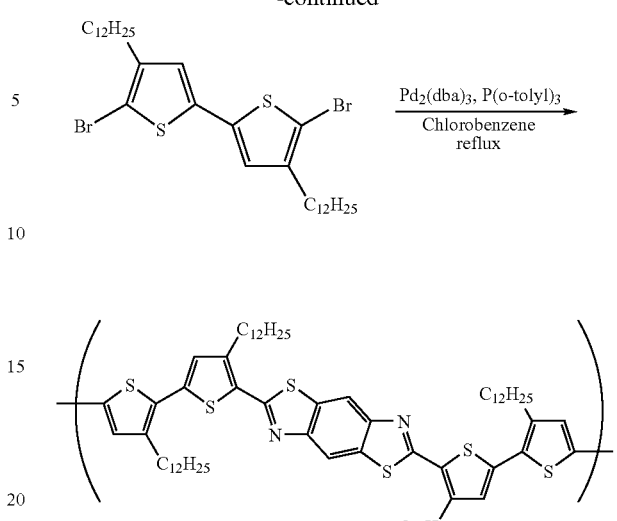

The following components were fed into a 50 ml three-necked flask containing a magnetic stirrer therein.

| | |
|---|---:|
| Bithiophene dibromo compound | 660.7 mg |
| | (2.0 mM) |
| Above-prepared benzobisthiazoleditrimethyltin compound | 1018.8 mg |
| | (1.0 mM) |
| Dried chlorobenzene | 25.2 ml |
| (i.e., 15 ml × total weights (1.6795 g) of the compounds used) | |

The mixture was subjected to argon bubbling.

Next, 18.3 mg (2 mol %) of Pd$_2$(dba)$_3$ and 24.3 mg (8 mol %) P(o-tolyl)$_3$ were added thereto, and the mixture was further subjected to argon bubbling for 10 minutes. Further, the mixture was subjected to a heat/reflux treatment for 2.5 hours using an oil bath heated to 145° C. The reaction product was then dispersed in a mixture solvent including 1000 ml of methanol and 25 ml of hydrochloric acid, and the dispersion was agitated for 8 hours. After the dispersion was filtered, the reaction product was subjected to a Soxhlet extract using methanol for 5 hours, followed by a Soxhlet extract using hexane for 12 hours and another Soxhlet extract using chlorobenzene. The thus prepared condensed liquid was then dispersed in 1000 ml of methanol. Thus, 1.12 g of a brown-colored solid compound was obtained. The yield was 94%.

The thus-prepared compound was dissolved in tetrahydrofuran, followed by filtering using a filter having openings of 0.45 μm. When the molecular weight of the compound was determined by gel permeation chromatography (GPC), it was confirmed that the compound has a polystyrene-conversion number average molecular weight of greater than 4200 and a polystyrene-conversion weight average molecular weight of greater than 5300.

Figure 10:
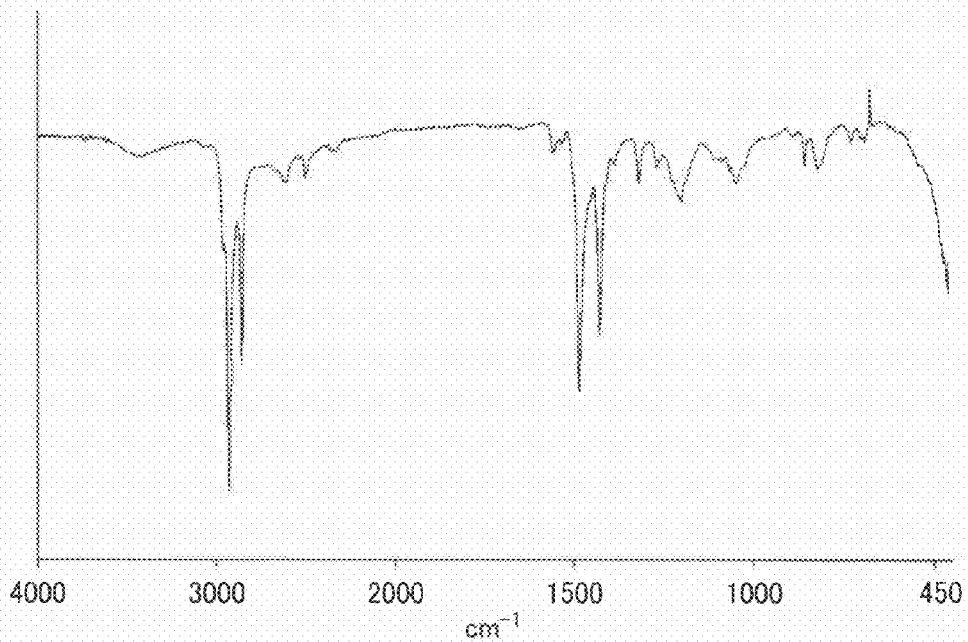
FIG. 10 is the IR spectrum of a third example of the polymer of the present invention prepared by using the benzobisthiazole compound.

The IR spectrum of the thus synthesized compound obtained by using KBr is illustrated in FIG. 10.

Comparative Application Example 1

Synthesis of Benzobisthiazole Boronic Acid Ester

The polymer of the present invention was prepared by a conventional synthesis method.
The reaction formula is as follows.

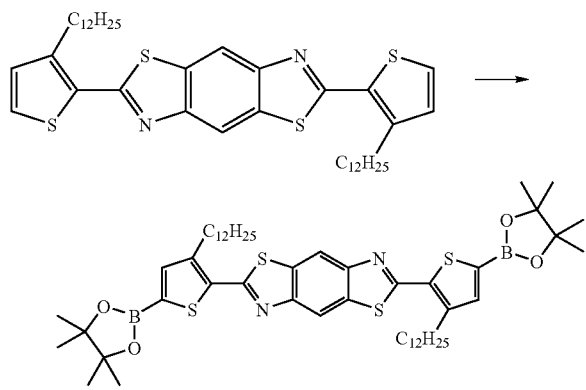

At first, 1.52 g of 2,6-bis(3-dodecylthiophene-2-yl)-benzo[1,2-d; 4,5-d']-bisthiazole was mixed with 150 ml of dehydrated tetrahydrofuran, and the mixture was cooled to −78° C. After 2 equivalent weight of tetramethylenediamine (TMEDA) and 2 equivalent weight of n-butyl lithium were added to the mixture, the mixture was agitated for 30 minutes at the temperature (−78° C.), followed by further agitation for 2 hours at room temperature. Next, 1.36 ml of 2-isopropoxy-4,4,5,5-tetramethyl-1,3,2-dioxaboralane was dropped thereinto, and the mixture was agitated for 1.5 hours. After being subjected to extraction using ethyl acetate, the reaction product was subjected to recrystallization using a mixture solvent of ethyl acetate and methanol twice, followed by short-path column chromatograph using florisil silica. The reaction product was then subjected to recrystallization using a mixture solvent of ethyl acetate and methanol. Thus, 1.07 g of the target compound was prepared. It was confirmed that the compound has a melting point of from 107 to 114° C.

The NMR Data of the Compound are as Follows.

$^1$H-NMR (CDCl$_3$, 400 MHz) δ0.88 (t, 6H, J=8 Hz), 1.22-1.56 (m, 60H), 1.76 (quint, 4H), 3.10 (t, 4H, J=8 Hz), 7.53 (s, 2H), 8.50 (s, 2H).

The above-prepared compound was reacted as follows.

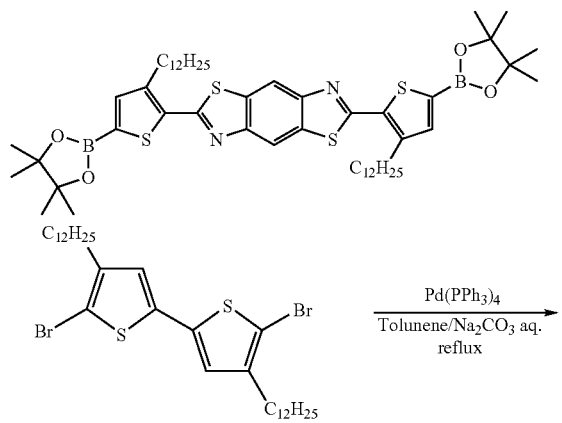

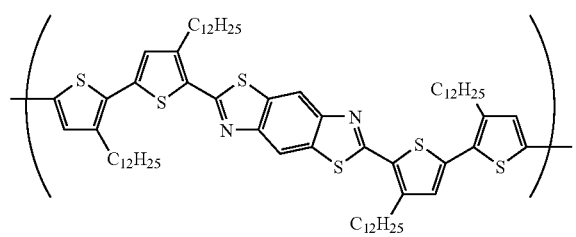

Specifically, the following components were mixed.

| | |
|---|---|
| Above-prepared diboronic acid ester compound | 472 mg |
| | (0.5 mM) |
| Bithiophene dibromo compound | 330 mg |
| | (0.5 mM) |
| Toluene | 3.5 ml |
| 2M aqueous solution of Na$_2$CO$_3$ | 1 ml |
| ALIQUANT ® 336 (tricaprylmethylammonium chloride serving as a phase transfer catalyst, from Sigma Aldrich Corp.) | 15 mg |

Next, 43.4 mg of Pd(0) (PPh$_3$) was added thereto. The mixture was agitated for 14 hours at 95° C. The reaction product was dispersed in a mixture solvent including 450 ml of methanol and 50 ml of ion exchange water, followed by washing with methanol and water. After being subjected to Soxhlet extract for 18 hours using acetone, followed by Soxhlet extract using chloroform, the reaction product was condensed such that the amount of chloroform decreases to about 15 ml. Then solution was dispersed in 600 ml of methanol, followed by filtering. The thus filtered material was dissolved in chloroform, followed by washing with ion-exchange water and recrystallization using methanol. Thus, the target polymer was prepared. The weight of the dried target polymer was 45 mg, and the yield was as low as about 8%.

The IR spectrum of the polymer is illustrated in FIG. 11.

When the molecular weight of the polymer was determined by gel permeation chromatography (GPC), it was confirmed that the polymer has a polystyrene-conversion number average molecular weight of 2100 and a polystyrene-conversion weight average molecular weight of 2400. Namely, the polymerization reaction hardly proceeded. As a result of the present inventors' study, it was found that the reason why the polymerization reaction hardly proceeded is that the boronic acid ester substituent is easily released from the compound due to alkali and heat.

This document claims priority and contains subject matter related to Japanese Patent Applications Nos. 2008-011190 and 2008-221131, filed on Jan. 22, 2008, and Aug. 29, 2008, respectively, incorporated herein by reference.

Having now fully described the invention, it will be apparent to one of ordinary skill in the art that many changes and modifications can be made thereto without departing from the spirit and scope of the invention as set forth therein.

What is claimed as new and desired to be secured by Letters Patent of the United States is:

1. A benzobisthiazole polymer comprising a unit having the following formula (2):

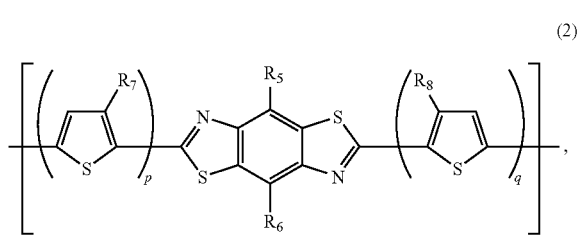

(2)

wherein each of $R_5$, $R_6$, $R_7$ and $R_8$ is a hydrogen atom, a halogen atom, a substituted or unsubstituted alkyl group, a substituted or unsubstituted alkoxyl group or a substituted or unsubstituted thioalkoxyl group, wherein at least one of $R_5$, $R_6$, $R_7$ and $R_8$ is not a hydrogen atom; and p and q are a same positive integer of 2 or more, wherein each of $R_7$ is the same as or different from the others, and each of $R_8$ is the same as or different from the others.

2. An organic film comprising the polymer according to claim 1.

3. The organic film according to claim 2, wherein the organic film has stereoregularity.

4. An organic thin-film transistor comprising:
an organic semiconductor layer including the organic film according to claim 2;
a pair of electrodes configured to flow an electric current through the organic semiconductor layer; and
a third electrode configured to apply a voltage to the organic semiconductor layer.

5. The benzobisthiazole polymer having a structure

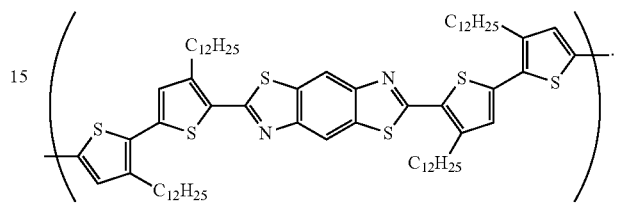

6. The organic film according to claim 2, wherein said organic film is subjected to a heat treatment at a temperature of not lower than 80° C.

* * * * *